United States Patent
Madhuranthakam et al.

(10) Patent No.: US 11,852,706 B2
(45) Date of Patent: Dec. 26, 2023

(54) SYSTEM AND METHOD FOR FAST T2-WEIGHTED MR IMAGING WITH FAT AND FLUID SUPPRESSION

(71) Applicant: BOARD OF REGENTS, THE UNIVERSITY OF TEXAS SYSTEM, Austin, TX (US)

(72) Inventors: Ananth J. Madhuranthakam, Coppell, TX (US); Robert E. Lenkinski, Dallas, TX (US); Xinzeng Wang, Dallas, TX (US); Ivan Pedrosa, Dallas, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 723 days.

(21) Appl. No.: 16/967,894

(22) PCT Filed: Feb. 8, 2019

(86) PCT No.: PCT/US2019/017152
§ 371 (c)(1),
(2) Date: Aug. 6, 2020

(87) PCT Pub. No.: WO2019/157246
PCT Pub. Date: Aug. 15, 2019

(65) Prior Publication Data
US 2021/0055364 A1     Feb. 25, 2021

Related U.S. Application Data

(60) Provisional application No. 62/628,046, filed on Feb. 8, 2018.

(51) Int. Cl.
*G01R 33/48* (2006.01)
*A61B 5/00* (2006.01)
(Continued)

(52) U.S. Cl.
CPC ........ *G01R 33/4828* (2013.01); *A61B 5/0036* (2018.08); *A61B 5/055* (2013.01);
(Continued)

(58) Field of Classification Search
CPC .. G01R 33/4828; G01R 33/5607; A61B 5/055
See application file for complete search history.

(56) References Cited

U.S. PATENT DOCUMENTS

| 8,143,889 B2 | 3/2012 | Jeong et al. |
| 8,229,544 B2 | 7/2012 | Tseng et al. |

(Continued)

FOREIGN PATENT DOCUMENTS

WO     2019157246 A1     8/2019

OTHER PUBLICATIONS

Antoch, et al. "Accuracy of whole body dual-modality fluorine-18-2-fluoro-2-deoxy-D-glucose positron emission tomography and computed tomography (FDG-PET/CT) for tumor staging in solid tumors: comparison with CT and PET" J Clin Oncol 2004;22(21):4357-4368.

(Continued)

*Primary Examiner* — Jason M Ip
(74) *Attorney, Agent, or Firm* — Edwin S. Flores; Daniel J. Chalker; Chalker Flores, LLP

(57) ABSTRACT

The present invention includes a method and apparatus for improved magnetic resonance imaging with simultaneous fat and fluid suppression of a subject comprising: acquiring four images, in-phase (IP) and out-of-phase (OP) at a short and a long echo time (TE) using a single-shot turbo spin echo from one or more magnetic resonance imager excitations: processing at least a pair of IP and OP images at a short and a long TE using single-shot turbo spin echo using a Dixon reconstruction; processing the pair of IP and OP images; subtracting the long TE water-only image from the (Continued)

shared-field-map Dixon reconstruction from the short TE water-only image to provide a fluid attenuation; processing water-only and fat-only images at the short and long TE to generate quantitative fat-fraction map; and reconstructing one or more 3D magnetic resonance images.

18 Claims, 10 Drawing Sheets

(51) Int. Cl.
    A61B 5/055     (2006.01)
    G01R 33/56     (2006.01)
    A61B 17/32     (2006.01)
    A61B 18/02     (2006.01)
    A61B 18/00     (2006.01)

(52) U.S. Cl.
    CPC ..... *G01R 33/5602* (2013.01); *G01R 33/5607* (2013.01); *A61B 18/02* (2013.01); *A61B 2017/320069* (2017.08); *A61B 2018/00577* (2013.01); *A61B 2018/00791* (2013.01)

(56) References Cited

U.S. PATENT DOCUMENTS

| | | |
|---|---|---|
| 8,692,551 B2 | 4/2014 | He et al. |
| 8,704,518 B2 | 4/2014 | Alsop et al. |
| 9,192,790 B2 | 11/2015 | Hastings et al. |
| 9,259,290 B2 | 2/2016 | Jenkins et al. |
| 2017/0146624 A1 | 5/2017 | Paul et al. |

OTHER PUBLICATIONS

Badve, et al. "MR Fingerprinting of Adult Brain Tumors: Initial Experience" Am J Neuroradiol 2017;38(3):492-499.
Berglund, et al. "Two-point dixon method with flexible echo times" Magn Reson Med 2011;65(4):994-1004.
Busse, et al. "Effects of refocusing flip angle modulation and view ordering in 3D fast spin echo" Magn Reson Med 2008;60(3):640-649.
Del Grande, et al. "Fat-suppression techniques for 3-T MR imaging of the musculoskeletal system" Radiographics 2014;34(1):217-233.
Eggers, et al. "Dual-echo Dixon imaging with flexible choice of echo times" Magn Reson Med 2011;65(1):96-107.
Eiber, et al. "Whole-body MRI including diffusion-weighted imaging (DWI) for patients with recurring prostate cancer: Technical feasibility and assessment of lesion conspicuity in DWI" J Magn Reson Imaging 2011;33(5):1160-1170.
Gold, et al. "Musculoskeletal MRI at 3.0 T: relaxation times and image contrast" Am J Roentgenol 2004;183(2):343-351.
Jackson, et al. "Combined fat-and water-suppressed MR imaging of orbital tumors" Am J Neuroradiol 1999;20(10):1963-1969.
Jambor, et al. "Prospective evaluation of planar bone scintigraphy, SPECT, SPECT/CT, 18F-NaF PET/CT and whole body 1.5 T MRI, including DWI, for the detection of bone metastases in high risk breast and prostate cancer patients: SKELETA clinical trial" Acta Oncol 2016,55(1):59-67.
Koh, et al. "Whole-body diffusion-weighted MRI: tips, tricks, and pitfalls" Am J Roentgenol, Aug. 2012; 199 (2):252-262.
Kwee, et al. "Diffusion-weighted whole-body imaging with background body signal suppression (DWIBS): features and potential applications in oncology" Eur Radiol 2008;;(published online Apr. 30, 2008) 18(9): 1937-1952.
Latifoltojar, et al. "Whole-body MRI quantitative biomarkers are associated significantly with treatment response in patients with newly diagnosed symptomatic multiple myeloma following bortezomib induction" Eur Radiol 2017,27:5325-36.
Lauenstein, et al. "Evaluation of optimized inversion-recovery fat-suppression techniques for T2-weighted abdominal MR imaging" J Magn Reson Imaging 2008;27(6):1448-1454.
Lavdas, et al. "Apparent diffusion coefficient of normal abdominal organs and bone marrow from whole-Body DWI at 1.5 T: the effect of sex and age" Am J Roentgenol, Aug. 2015; 205(2):242-250.
Loening, et al. "Increased speed and image quality in single-shot fast spin echo imaging via variable refocusing flip angles" J Magn Reson Imaging , Jun. 2015;42(6):1747-1758.
Lu, et al. "Quantitative evaluation of oxygenation in venous vessels using T2-Relaxation-Under-Spin-Tagging MRI" Magn Reson Med 2008;60(2):357-363.
Madhuranthakam, et al. "Improved short tau inversion recovery (iSTIR) for increased tumor conspicuity in the abdomen" Magn Reson Mater Phy 2014;27(3):245-255.
Padhani, et al. "Whole-Body Dffusion-weighted MR imaging in cancer: Current Status and Research Directions" Radiology, Dec. 2011;261(3):700-718.
Park, et al. "A prospective evaluation of 18F-FDG and 11C-acetate PET/CT for detection of primary and metastatic hepatocellular carcinoma" J Nucl Med 2008;49(12):1912-1921.
Punwani, et al. "Pediatric and Adolescent Lymphoma: Comparison of Whole-Body STIR Half-Fourier Rare MR Imaging with an Enhanced PET/CT Reference for Initial Staging 1" Radiology 2010;255(1):182-190.
Sarkar, et al. "Brain MR imaging at ultra-low radiofrequency power" Radiology, Published online May 1, 2011;259(2):550-557.
Schöder, et al. "Screening for cancer with PET and PET/CT: potential and limitations" J Nucl Med, Jan. 2007;48 (1 suppl):4S-18S.
Smith, et al. "Measurement of T1 and T2 in the cervical spinal cord at 3 tesla" Magn Reson Med, Jul. 2008,60(1):213-219.
Stanisz, et al. "T1, T2 relaxation and magnetization transfer in tissue at 3T" Magn Reson Med 2005;54(3):507-512.
Takenaka, et al. "Detection of bone metastases in non-small cell lung cancer patients: Comparison of whole-body diffusion-weighted imaging (DWI), whole-body MR imaging without and with DWI, whole-body FDG-PET/CT, and bone scintigraphy" J Magn Reson Imaging, Jul. 23, 2009,30(2):298-308.
United States Patent and Trademark Office/ISA—International Search Report and the Written Opinion for PCT/US2019/017152 dated Apr. 23, 2019, 9 pp.
Walker, et al. "Turbo STIR magnetic resonance imaging as a whole-body screening tool for metastases in patients with breast carcinoma: Preliminary clinical experience" J Magn Reson Imaging, Apr. 13, 2000;11(4):343-350.
Wang, et al. "MR Neurography of Brachial Plexus at 3.0 T with Robust Fat and Blood Suppression" Radiology, May 2017;283(2):538-546.

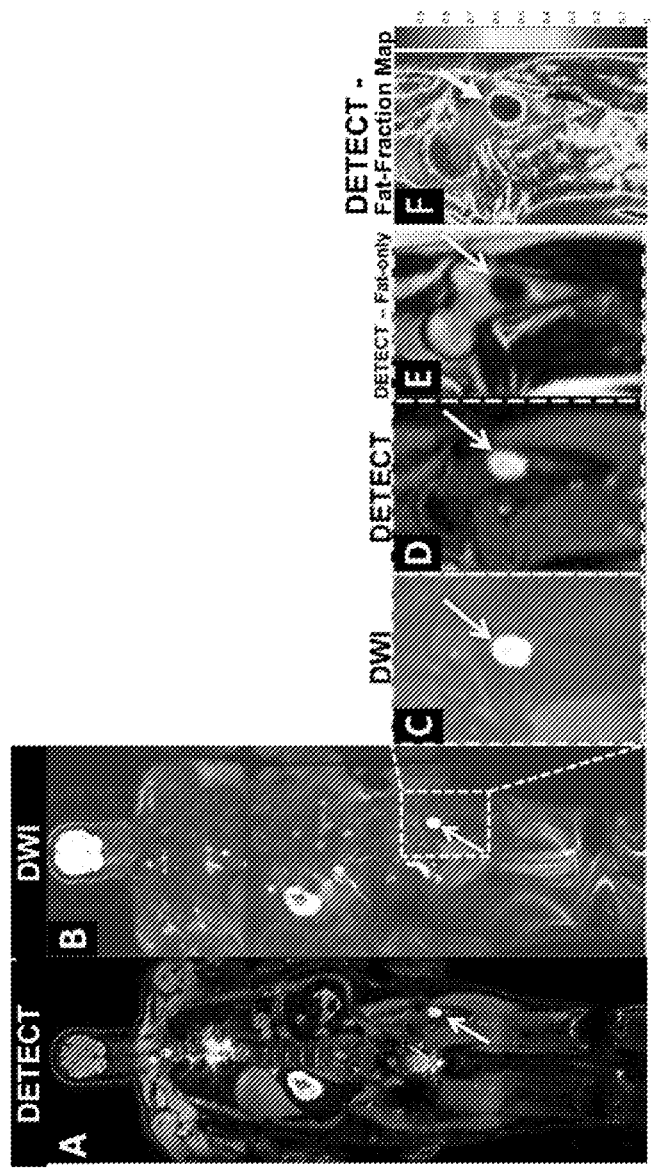

SYSTEM AND METHOD FOR FAST T2-WEIGHTED MR IMAGING WITH FAT AND FLUID SUPPRESSION

CROSS-REFERENCE TO RELATED APPLICATIONS

This application is a National Stage of International Application No. PCT/US2019/017152, filed Feb. 8, 2019, which claims the benefit of U.S. Provisional Application No. 62/628,046, filed Feb. 8, 2019. The contents of each of which are incorporated by reference in their entirety.

STATEMENT OF FEDERALLY FUNDED RESEARCH

This invention was made with government support under P50CA196516 and U01CA207091 awarded by National Cancer Institute of National Institutes of Health (NIH/NCI). The government has certain rights in the invention.

TECHNICAL FIELD OF THE INVENTION

The present invention relates in general to the field of imaging techniques using magnetic resonance imaging for whole-body cancer detection, followed by characterization of selected tumors by dedicated functional MR imaging as well as for real-time monitoring of ablation volume in MR guided ablation therapies.

BACKGROUND OF THE INVENTION

Without limiting the scope of the invention, its background is described in connection with imaging.

Whole-body imaging using conventional techniques such as positron emission tomography combined with computed tomography (PET/CT) is routinely used clinically for whole-body cancer detection (1). A major concern with these techniques is the exposure to ionizing radiation (2-4), particularly in younger patients who need repeated exposures during long follow-up periods and staging in patients during post-treatment. Additionally, the spatial resolution of PET is limited and some tumors do not demonstrate uptake consistently with conventional radiotracers resulting in very low sensitivities reported for a variety of tumors, particularly when lesions are of smaller size (<1 cm) (5,6). Moreover, while these limitations may be partially compensated with contrast-enhanced computed tomography (CT) examinations, this leads to additional radiation exposure. Furthermore, repeated administrations of nephrotoxic iodinated contrast agents with CT is undesirable in patients with impaired renal function (7), a common occurrence in patients with metastatic disease.

In the past decade, whole-body magnetic resonance imaging (WB-MRI) has become a valuable alternative technique due to its excellent soft tissue contrast combined with high spatial resolution and the lack of ionizing radiation (8). WB-MRI, particularly using echo-planar based diffusion-weighted imaging (DW-EPI), and diffusion weighted imaging with background suppression (DWIBS), have shown improved sensitivity and specificity for metastatic cancer detection at 1.5 T (9). DWI offers increased conspicuity for lesions with restricted diffusion (e.g. high cellularity) by suppressing the confounding tissue signals such as fat and fluid (10,11).

However, DWI techniques that rely on EPI sequences suffer from geometric distortions due to large $B_0$ inhomogeneities, particularly using large field-of-views (FOV), such as during whole body imaging. Moreover, diffusion weighted imaging (DWI) is inherently signal-to-noise ratio (SNR) limited. Consequently, DWI acquisitions require reduced spatial resolution, multiple signal averages, or both, which results in an increase of the total scan time (10). While the inherent low SNR can be partly mitigated by performing WB-MRI at 3 T, larger $B_0$ inhomogeneities at 3 T compared to 1.5 T lead to worse geometric distortions (12). Alternatively, WB-MRI using short tau inversion recovery (STIR) has been shown to provide increased tumor conspicuity with limited image distortion (13,14). However, STIR also suffers from reduced SNR due to non-selective inversion and requires multiple signal averages resulting in increased total scan times (15).

Furthermore, most metastatic lesions tend to have longer T2 relaxivity compared to their surrounding non-neoplastic tissues and therefore appear brighter on T2-weighted (T2W) images. However, fat has relatively long T2 relaxivity and fluid has very long T2 relaxivity and therefore, both also appear bright on most clinical T2W images and need to be suppressed to improve lesion conspicuity (16,17). T2W images with fat suppression, either using STIR or chemically selective suppression such as spectral pre-saturation using (adiabatic) inversion recovery (SPIR/SPAIR) (18), can generate fat-suppressed T2W images, but still carry fluid signal such as in cysts that often mimic lesions. Furthermore, STIR suffers from poor SNR, while SPIR/SPAIR suffers from inhomogeneous fat suppression particularly at 3 T due to increased $B_0$ inhomogeneities (12,15).

Despite these advances, a need remains for a whole-body MRI technique at 3 T with improved lesion conspicuity for metastatic cancer detection that is fast and provides a high-resolution, with an improved signal-to-noise ratio (SNR).

SUMMARY OF THE INVENTION

In one embodiment, the present invention includes a method for improved magnetic resonance imaging with simultaneous fat and fluid suppression of a subject comprising: acquiring four images, in-phase (IP) and out-of-phase (OP) at a short and a long echo time (TE) using a single-shot turbo spin echo from one or more magnetic resonance imager excitations: processing at least a pair of in-phase (IP) and out-of-phase (OP) images at a short and a long echo time (TE) using single-shot turbo spin echo using a Dixon reconstruction; processing at least a pair of in-phase (IP) and out-of-phase (OP) images at a short and a long echo time (TE) using single-shot turbo spin echo using a shared-field-map Dixon reconstruction; subtracting the long TE water-only image from the shared-field-map Dixon reconstruction from the short TE water-only image from the Dixon reconstruction to provide a fluid attenuation; and may optionally include processing water-only and fat-only images at the short and long TE to generate quantitative fat-fraction map; and reconstructing one or more magnetic resonance images from the acquired data sets to provide one or more 3D magnetic resonance images. In one aspect, the magnetic resonance images of a single slice are acquired in less than one second. In another aspect, the magnetic resonance images are acquired with a 1.5 T or 3 T magnetic resonance imager. In another aspect, the images are whole body images. In another aspect, the images may comprise cancer lesions. In another aspect, a processing time for a fluid attenuated whole body image is less than 16, 15, 14, 13, 12, 11, 10, 9, 8, or 7 minutes. In another aspect, the 3D magnetic resonance images have an improved signal-to-noise ratio when $B_0$ inhomogeneities are present. In another aspect, each pair of in-phase (IP) and out-of-phase (OP) images are captured after a single 90° excitation pulse, with a short TE (TE1, ~60-80 ms) and long TE (TE2, ~400 ms). In another aspect, the method further comprises capturing echoes between each pair of refocusing pulses for each pair of in-phase (IP) and out-of-phase (OP) images. In another aspect, each pair of in-phase (IP) and out-of-phase (OP) images are acquired in a single repetition using variable refocusing flip angles and partial phase-encoding acquisitions using a single shot turbo spin echo. In another aspect, the method further comprises creating a shared-field-map mDixon reconstruction in which a $B_0$ map estimated at the short TE is used for fat/water separation at the long TE. In another aspect, the method further comprises an adaptive complex subtraction of the long TE water-only image from the short TE water-only image to achieve fluid attenuation. In another aspect, the method simultaneously suppresses fat and fluid in the images. In another aspect, the method further comprises of dividing the fat-only image by the sum of water-only and fat-only image at short TE and long TE to generate quantitative fat-fraction map. In another aspect, a magnetic resonance image is interleaved with real-time temperature measurement for accurate monitoring of MRI guided ablation therapies. In another aspect, a long TE water-only image shows ablation volume in MRI guided ablation therapies.

In another embodiment, the present invention includes a method of three dimensional (3D) dynamic magnetic resonance imaging of an imaging space comprising: placing a subject into a substantially homogeneous magnetic field in the imaging space of a magnetic resonance imager; acquiring four images, in-phase (IP) and out-of-phase (OP) at a short and a long echo time (TE) using a single-shot turbo spin echo from one or more magnetic resonance imager excitations: processing at least a pair of in-phase (IP) and out-of-phase (OP) images at a short and a long echo time (TE) using single-shot turbo spin echo using a Dixon reconstruction; processing at least a pair of in-phase (IP) and out-of-phase (OP) images at a short and a long echo time (TE) using single-shot turbo spin echo using a shared-field-map Dixon reconstruction; subtracting the long TE water-only image from the shared-field-map Dixon reconstruction from the short TE water-only image from the Dixon reconstruction to provide a fluid attenuation; processing water-only and fat-only images at the short and long TE to generate quantitative fat-fraction map; and reconstructing one or more magnetic resonance images from the acquired data sets to provide one or more 3D magnetic resonance images. In one aspect, the magnetic resonance images of a single slice are acquired in less than one second. In another aspect, the magnetic resonance images are acquired with a 1.5 T or 3 T magnetic resonance imager. In another aspect, the e images are whole body images. In another aspect, the images comprise cancer lesions. In another aspect, a processing time for a fluid attenuated whole body image is less than 16, 15, 14, 13, 12, 11, 10, 9, 8, or 7 minutes. In another aspect, the 3D magnetic resonance images have an improved signal-to-noise ratio when $B_0$ inhomogeneities are present. In another aspect, each pair of in-phase (IP) and out-of-phase (OP) images are captured after a single 90° excitation pulse, with a short TE (TE1, ~60-80 ms) and long TE (TE2, ~400 ms). In another aspect, the method further comprises capturing echoes between each pair of refocusing pulses for each pair of in-phase (IP) and out-of-phase (OP) images. In another aspect, each pair of in-phase (IP) and out-of-phase (OP) images are acquired in a single repetition using variable refocusing flip angles and partial phase-encoding acquisitions using a single shot turbo spin echo. In another aspect, the method further comprises creating a shared-field-map mDixon reconstruction in which a $B_0$ map estimated at the short TE is used for fat/water separation at the long TE. In another aspect, the method further comprises an adaptive complex subtraction of the long TE water-only image from the short TE water-only image to achieve fluid attenuation. In another aspect, the method simultaneously suppresses fat and fluid in the images. In another aspect, the method further comprises of dividing the fat-only image by the sum of water-only and fat-only image at short TE and long TE to generate quantitative fat-fraction map. In another aspect, a magnetic resonance image is interleaved with real-time temperature measurement for accurate monitoring of MRI guided ablation therapies. In another aspect, a long TE water-only image shows ablation volume in MRI guided ablation therapies.

In another embodiment, the present invention includes a computerized method of three dimensional (3D) dynamic magnetic resonance imaging, the method comprising: acquiring four images, in-phase (IP) and out-of-phase (OP) at a short and a long echo time (TE) using a single-shot turbo spin echo from one or more magnetic resonance imager excitations, and using a processor; processing at least a pair of in-phase (IP) and out-of-phase (OP) images at a short and a long echo time (TE) using single-shot turbo spin echo using a Dixon reconstruction; processing at least a pair of in-phase (IP) and out-of-phase (OP) images at a short and a long echo time (TE) using single-shot turbo spin echo using a shared-field-map Dixon reconstruction; subtracting the long TE water-only image from the shared-field-map Dixon reconstruction from the short TE water-only image from the Dixon reconstruction to provide a fluid attenuation; processing water-only and fat-only images at the short and long TE to generate quantitative fat-fraction map; and reconstructing one or more magnetic resonance images from the acquired data sets to provide one or more 3D magnetic resonance images.

In another embodiment, the present invention includes a system for three dimensional (3D) dynamic magnetic resonance imaging, the system comprising: a magnetic resonance imager capable of generating a substantially homogeneous magnetic field in an imaging space and capable of detecting a subject for magnetic resonance imaging; a processor comprising a non-transitory computer readable medium comprising instructions stored thereon for: acquiring four images, in-phase (IP) and out-of-phase (OP) at a short and a long echo time (TE) using a single-shot turbo spin echo from one or more magnetic resonance imager excitations, and using a processor; processing at least a pair of in-phase (IP) and out-of-phase (OP) images at a short and a long echo time (TE) using single-shot turbo spin echo using a Dixon reconstruction; processing at least a pair of in-phase (IP) and out-of-phase (OP) images at a short and a long echo time (TE) using single-shot turbo spin echo using a shared-field-map Dixon reconstruction; subtracting the long TE water-only image from the shared-field-map Dixon reconstruction from the short TE water-only image from the Dixon reconstruction to provide a fluid attenuation; processing water-only and fat-only images at the short and long TE to generate quantitative fat-fraction map; and reconstructing one or more magnetic resonance images from the acquired data sets to provide one or more 3D magnetic resonance images; wherein the processor reconstructs the magnetic resonance images from the acquired data sets to provide a set of 3D magnetic resonance images with a processor, wherein the 3D magnetic resonance images are obtained without increasing sensitivity to $B_0$ inhomogeneities, and simultaneously suppressing fat and fluid in the images; and storing on the computer or in the one or more databases or displaying on a communications interface, the 3D magnetic resonance images.

BRIEF DESCRIPTION OF THE DRAWINGS

For a more complete understanding of the features and advantages of the present invention, reference is now made to the detailed description of the invention along with the accompanying figures and in which:

FIGS. 8A to 8F show whole-body MRIs of a 64-year old male patient volunteer with advanced renal cell carcinoma showing improved lesion localization and quantitative fat-fraction map capabilities of DETECT. While both DETECT (FIG. 8A) and DWIBS (FIG. 8B) images show a left lower extremity lesion (arrows), the DWIBS image cannot localize the finding to bone, muscle or lymph node, even when zoomed in (FIG. 8C, arrow). However, DETECT clearly localizes the lesion within the left femur (FIG. 8A, FIG. 8D; arrows). (FIG. 8E) DETECT fat-only image, acquired in the same sequence, confirms the loss of normal marrow (arrow), increasing diagnostic confidence for both location and malignant nature of this lesion. Using water-only image (FIG. 8D) and fat-only image (FIG. 8E), DETECT allows the generation of quantitative fat-fraction map (FIG. 8F).

DETAILED DESCRIPTION OF THE INVENTION

Figure 1:
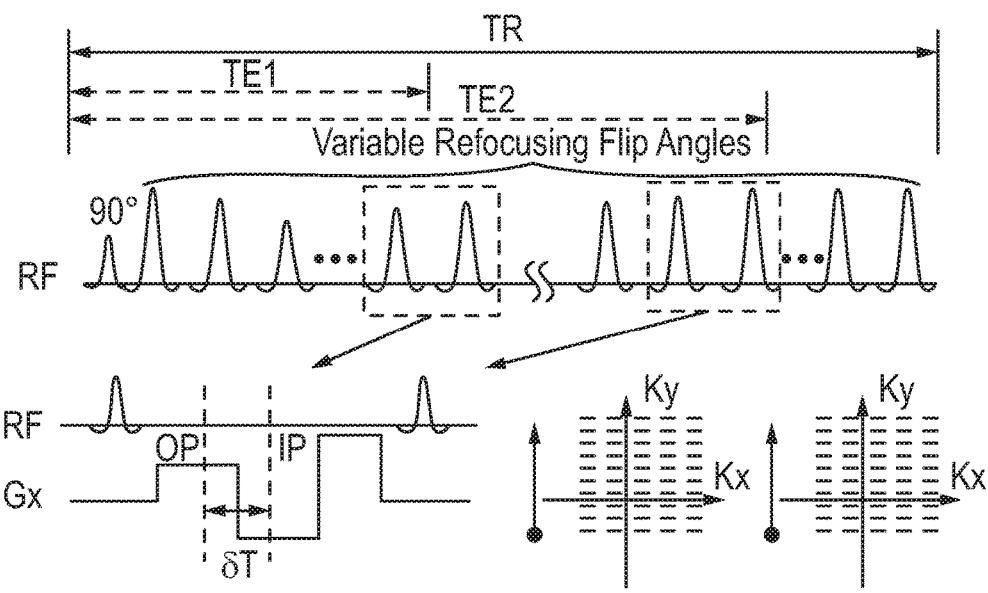
FIG. 1. Schematic of the Dual Echo T2-weighted acquisition for Enhanced Conspicuity of Tumors (DETECT) using single-shot turbo spin echo. In each repetition, four images are acquired using variable refocusing flip angles, including out-of-phase (OP) and in-phase (IP) images at both short TE (TE1) and long TE (TE2). The IP and OP echoes are acquired using the bipolar readout gradients (Gx) with partial echo acquisitions between each pair of refocusing pulses, and at all refocusing pulses. After the readout gradients, a rewinder gradient with large gradient strength is used to minimize the echo spacing. St is the time difference between the OP and IP acquisitions (e.g. 1.1 ms at 3 T). For both TEs, a linear view-ordering with partial phase encoding is used to sample the k-space.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The present inventors developed a fast, high-resolution and high signal-to-noise ratio T2-weighted (T2W) MR imaging technique with simultaneous fat and fluid suppression, for whole-body imaging at 3 T with improved lesion conspicuity for metastatic cancer detection, generation of quantitative fat-fraction map or to provide real-time ablation volumes that can be interleaved with real-time temperature monitoring in MRI guided ablation therapies.

The Dual-Echo T2-weighted acquisition for Enhanced Conspicuity of Tumors (DETECT) acquires four images, in-phase (IP) and out-of-phase (OP) at a short and a long echo time (TE) using single-shot turbo spin echo. The IP/OP images at the short and long TEs are reconstructed using the standard Dixon and shared-field-map Dixon reconstruction respectively, for robust fat/water separation. An adaptive complex subtraction between the two TE water-only images achieves fluid attenuation. The water-only and fat-only images are used to generate quantitative fat-fraction map. DETECT imaging was optimized and evaluated in whole-body imaging of five healthy volunteers, and compared against diffusion-weighted imaging with background suppression (DWIBS) in five patients with known metastatic renal cell carcinoma.

It was possible to obtain robust fat/water separation and fluid attenuation, which was achieved using the shared-field-map Dixon reconstruction and adaptive complex subtraction, respectively. DETECT imaging technique generated co-registered T2W images with and without fat suppression, heavily T2W, fat and fluid suppressed T2W whole-body images, and quantitative fat-fraction map in less than 7 minutes. Compared to DWIBS acquired in 17 minutes, the DETECT imaging achieved better detection and localization of lesions in patients with metastatic cancer.

The new DETECT imaging technique generates T2W images with high resolution, high SNR, minimal geometric distortions, and provides good lesion conspicuity with robust fat and fluid suppression and quantitative fat-fraction map in less than 7 minutes for whole-body imaging, demonstrating efficient and reliable metastatic cancer detection at 3 T.

Imaging Sequence. The imaging strategy of the present invention is based on a single shot turbo spin echo (SShTSE), which is a routinely used T2W imaging sequence in the body due to its robustness, favorable SNR and minimal image distortion. SShTSE is often performed with fat suppression for improved lesion conspicuity, commonly using SPIR/SPAIR, due to its increased SNR compared to STIR. However, SPIR/SPAIR suffers from fat-suppression failures in areas with increased $B_0$ inhomogeneities, particularly relevant at 3 T. Moreover, when applied for whole-body imaging, the thoracic region is prone to fat-suppression failure due to increased $B_0$ inhomogeneities. To overcome these challenges, the inventors used a modified Dixon (mDixon) based SShTSE acquisition, which provided robust fat/water separation in the abdomen in a single acquisition (19). The inventors combined this SShTSE-mDixon with a dual-echo acquisition to achieve fluid suppression, see, e.g., U.S. Pat. No. 8,704,518 B2, relevant portions incorporated herein by reference. This sequence acquires two sets of images—one at a short echo time (TE) and the other at a long TE, following the same excitation. The non-neoplastic tissues with short T2 and the metastatic lesions with moderately prolonged T2 preferentially appear on the short TE image, while the fluids with very long T2 appear on both short and long TE images. Thus, subtraction of the long TE from the short TE preferentially suppresses fluid signal (20) and improves tumor conspicuity (21). The inventors refer to this technique as, Dual Echo T2-weighted acquisition for Enhanced Conspicuity of Tumors (DETECT).

FIG. 1 illustrates a schematic of the DETECT imaging sequence. Following a single 90 excitation pulse, short TE (TE1, ~60-80 ms) images and long TE (TE2, ~400 ms) images are acquired in the same repetition using variable refocusing flip angles (22) and partial phase-encoding acquisitions using a SShTSE. Between each pair of refocusing pulses, in-phase (IP) and out-of-phase (OP) echoes are acquired for both TEs, at all refocusing pulses, using a bipolar readout for mDixon reconstruction. Partial-echo readouts are implemented to balance the in-plane resolution and receiver bandwidth (RBW), while maintaining the optimal time interval ($\delta t$) of ~1.1 ms at 3 T between IP and OP echoes for robust fat/water separation (19,23). An echo train length (ETL) of ~130 was used for both TEs, with 65 k-space lines for each TE. The RBW of the DETECT sequence was doubled to ~870 Hz/pixel, compared to ~440 Hz/pixel for the standard SShTSE. However, the reconstruction of water-only images using signal averaging of both IP/OP echoes generated comparable images to the standard SShTSE (19). Overall, four images are acquired with both partial phase-encoding and partial readout in a single repetition, including IP and OP images at both short and long TEs using DETECT.

Image Reconstruction.

Fat suppression. A phase-preserved homodyne reconstruction was used to reconstruct the IP and OP images at both TEs, with zero-filling along the frequency-encoding direction and homodyne filtering along the phase-encoding direction (19,23). This facilitated the reconstruction of complex IP and OP images, which allowed standard mDixon reconstruction for fat/water separation (24). While this approach provided robust fat/water separated images at short TE, the fat/water separation was not as effective at long TE due to the reduced SNR. To overcome this problem, a shared-field-map mDixon reconstruction was used, in which the $B_0$ map estimated at the short TE was used for fat/water separation at the long TE. Considering that the $B_0$ map changes slowly and all images are acquired within the same repetition, this shared-field-map mDixon reconstruction generates robust fat/water separation at the long TE (25). The standard mDixon reconstruction for the short TE images was performed on the scanner including the generation of the low-pass filtered $B_0$ map. The shared-field-map mDixon reconstruction using this low-pass filtered $B_0$ map for the long TE images was implemented in Matlab (Mathworks, Natick, MA).

Fluid Attenuation. The water-only images reconstructed at the short TE ($W_{TE1}$) and the long TE ($W_{TE2}$) represent T2-weighted and heavily T2-weighted images respectively, with uniform fat suppression. Given that the tissues with very long T2 (e.g. CSF and gall bladder) appear hyper intense on both short and long TE images, a subtraction between these two images was performed to achieve fluid attenuation. Specifically, a complex subtraction, enabled by the phase-preserved homodyne reconstruction, including a scaling factor (f) was used to perform fluid attenuation (Eq. 1).

$$W_{sub} = \text{Real}[(W_{TE1} - f \times W_{TE2})e^{-i\psi_1}] \quad (1)$$

where $\psi_1$ is the phase of the $W_{TE1}$ image and $W_{sub}$ is the final subtracted water-only image with fat and fluid suppression. The scaling factor, f, was calculated using the following steps: First, the pixels that had signal intensities greater than 80% of the maximum signal intensity on the $W_{TE2}$ image were selected. Next, the same pixels on the $W_{TE1}$ image were identified. Finally, f was calculated as the mean value of the ratio of these pixels, i.e. $f = \text{mean}(I_1/I_2)$, where $I_1$ and $I_2$ are the signal intensities of the reference pixels in $W_{TE1}$ and $W_{TE2}$ respectively. This scaling factor compensated the T2 decay of tissues with long T2; however, it overcompensated for tissues with very long T2 (e.g. when abs($f \times W_{TE2}$) > abs($W_{TE1}$)). Thus, the demodulation of the phase, $\psi_1$, and the final real operation in equation 1 preserved the sign after the complex subtraction and rectified this overcompensation by resetting those pixel values to zero. The complex subtraction including the scaling factor calculation and phase demodulation was implemented in Matlab. Furthermore, the water-only image (W) and fat-only image (F) at either the short TE (TE1) or at the long TE (TE2) can be used to generate the quantitative fat-fraction (FF) map (Equation 2).

$$FF = \frac{F}{W + F} \quad (2)$$

Figure 9:
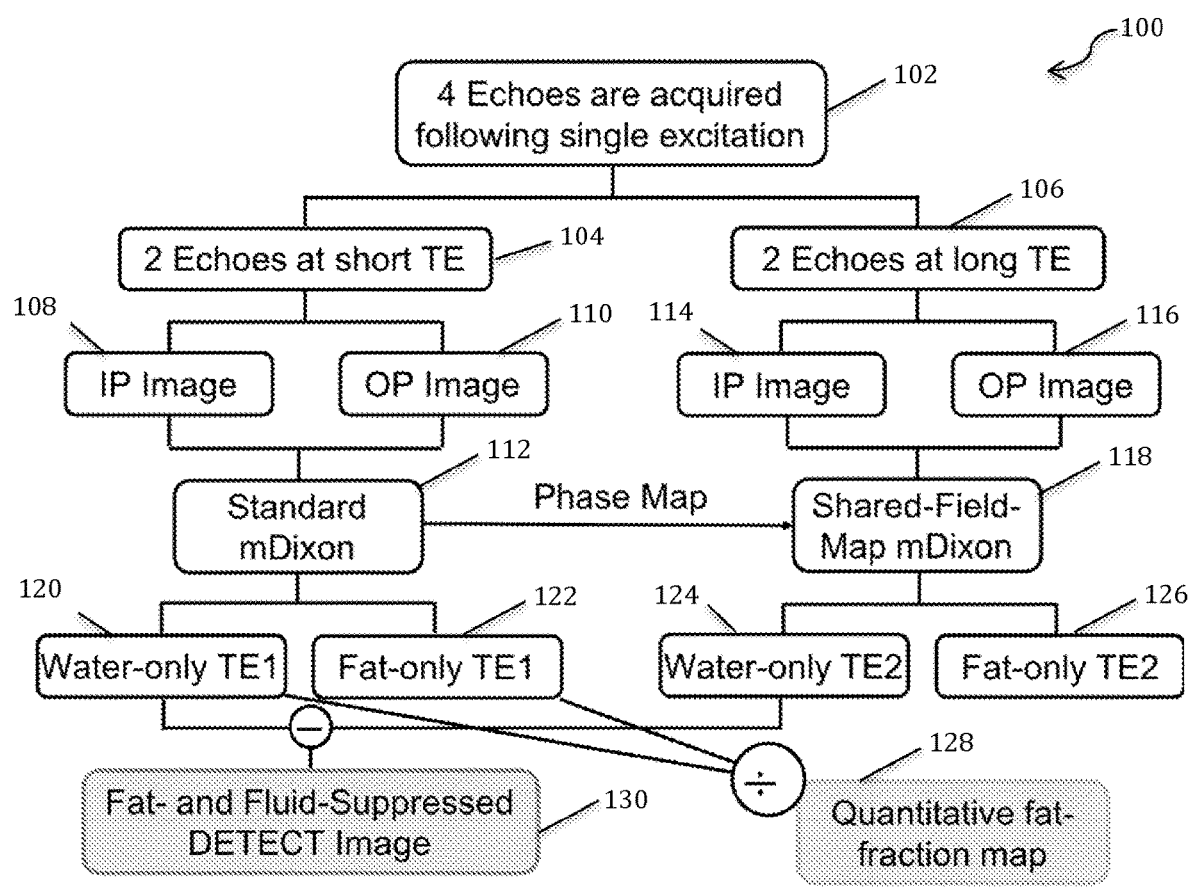
FIG. 9 shows a flowchart showing the DETECT reconstruction including fat and fluid suppression, and quantitative fat-fraction map generation.

A flowchart showing the DETECT reconstruction including fat and fluid suppression and quantitative fat-fraction map generation is shown in FIG. 9.

Simulations. The choice of the TEs determines the signal difference that can be achieved on the $W_{sub}$ image to enhance the conspicuity of the tumors, while simultaneously suppressing the fluids. Several factors of an SShTSE acquisition determine the TE, including view-ordering, echo spacing, FOV, partial phase-encoding factor and refocusing flip angle scheme. In this study, the inventors chose linear view-ordering and variable refocusing flip angle schemes (22) for both TEs, to match clinically used SShTSE acquisitions at short TE (i.e. TE1=60-80 ms) for T2-weighted imaging of the abdomen, while also reducing the total SAR. The variable refocusing flip angle scheme was defined by the minimum, and maximum refocusing flip angles ($\alpha_{min}$, $\alpha_{max}$), used to sample the beginning and end of the echo train respectively, along with the middle refocusing flip angle ($\alpha_{mid}$) used to sample the center of the k-space for short TE (26). The $\delta t$ of about 1.1 ms, combined with receiver bandwidth and in-plane resolution forced the minimum echo spacing to be about 6.6 ms. Thus, the effective echo time ($TE_{eff}$), defined as the TE when the center of k-space was sampled, and the equivalent echo time ($TE_{equv}$), defined as the TE that generates similar contrast as standard T2W image, were determined by the variable refocusing flip angle scheme in combination with the partial phase-encoding factor.

Bloch equation simulations were performed to investigate the influence of variable refocusing flip angle scheme and the partial phase-encoding factor on the signal difference to determine the optimal TEs. First, the partial phase-encoding factor was fixed at 0.6, similar to the standard clinical SShTSE acquisition, along with $\alpha_{min}$ at 90 and $\alpha_{max}$ at 180°, while the $\alpha_{mid}$ was varied from 100° to 160° at 20° increments. This achieved the following TE values: TE1=60 ms and TE2=450 ms. Next, the partial phase-encoding factor was varied between 0.6 and 0.7 (which also varied the TE1 and TE2 times), with the $\alpha_{min}$, $\alpha_{mid}$, $\alpha_{max}$ and a fixed at 90°, 100°, and 120° respectively. These flip angles were chosen to achieve clinically equivalent TE, while reducing the total SAR (27) and sensitivity to motion (23). The other simulations parameters were: FOV=520 mm (phase-encoding direction), voxel size=1.8 mm, SENSE=3, echo spacing=6.6 ms. Signal evolution was calculated for a variety of tissues with the following $T_1$ and $T_2$ values at 3 T (28-31): gray matter, $T_1/T_2$=1820/99 ms; white matter, $T_1/T_2$=1084/69 ms; liver, $T_1/T_2$=812/42 ms; kidney, $T_1/T_2$=1194/56 ms; fat, $T_1/T_2$=371/133 ms; synovial fluid, $T_1/T_2$=3620/767 ms; CSF, $T_1/T_2$=4500/2500 ms; and a generic tumor model with $T_1/T_2$=1000/150 ms. The signal differences between the two TEs were plotted against a range of T2 values.

Imaging Studies. All imaging was performed on a 3 T MR scanner (Ingenia, Philips Healthcare, Best, The Netherlands). The DETECT was evaluated in 6 healthy volunteers, first in a dedicated abdominal imaging session of a healthy volunteer, followed by whole-body imaging protocol in 5 healthy volunteers. Subsequently, 5 patients with known metastatic renal cell carcinoma (mRCC) were enrolled for whole-body imaging evaluation of the DETECT sequence. The study protocol was approved by the institutional review board (IRB), Health Insurance Portability and Accountability Act (HIPAA)-compliant and all subjects provided written informed consent prior to their participation in the study.

Abdominal Imaging. To evaluate the shared-field-map mDixon reconstruction, one 40-year old healthy female volunteer was enrolled for abdominal imaging. The acquisition parameters for the DETECT sequence were: coronal orientation; FOV=400×400 mm$^2$; slice thickness/slice gap=4 mm/0 mm; voxel size=1.5×2 mm$^2$; SENSE=3; echo spacing=6.2 ms; $TE_{eff}$/$TE2_{eff}$=69/340 ms; $TE_{equiv1}$/$TE_{equiv2}$=62/297 ms; TR=1250 ms; $\delta t$=1.1 ms; ETL=130 for both TEs with 65 k-space lines for each TE; RBW=~870 Hz/pixel; partial phase-encoding factor=0.65 and partial readout factor=0.7. A total of 42 slices were acquired with 14 slices each in a 16-second breath hold acquisition. A 16-channel phased-array anterior coil, along with the 12-channel phased-array posterior coil, embedded in the table, were used for signal reception.

Whole-Body Imaging of Normal Volunteers. Five healthy volunteers (3 females, 2 males, age range: 24-61 years), including 2 volunteers for optimization and 3 volunteers for evaluation of whole-body DETECT imaging were enrolled. The three healthy volunteers were scanned in 5 stations (head, thorax, abdomen, pelvis, and thighs) to cover the whole body from the head to the knees. All images were acquired in the coronal plane at an acquisition time of about 1 minute per station for approximately 50 slices. The thoracic and abdominal regions were acquired in four, 15-second breathhold acquisitions each, which increased the scan time to about 2 minutes for each of these stations, including the breathhold instructions. A SENSE acceleration factor of 3, partial phase-encoding factor of 0.6, partial readout factor of 0.85, ETL of 130 for both TEs with 65 k-space lines for each TE, RBW of 870 Hz/pixel and δt of 1.1 ms were used. All images were acquired contiguous with no slice gap. The remaining acquisition parameters are listed in Table 1. The total scan time of whole-body DETECT imaging was approximately 7 minutes including the breathhold instructions.

$$T2_{eff} = (TE_{2eff} - TE_{1eff}) / \log\left(\frac{W_{TE1}}{W_{TE2}}\right) \quad (2)$$

$$I_{T2w} = T2_{eff} \times W_{sub} \quad (3)$$

where $TE1_{eff}$ and $TE2_{eff}$ are the effective TEs.

Image Evaluation. In all 8 whole-body subjects, including 3 healthy volunteers and 5 mRCC patients, the signal reduction of long T2 tissues such as fluids on the DETECT sequence was measured compared to the short TE image, as described before (21). Additionally, the number of lesions identified on the proposed DETECT sequence compared to DWIBS was assessed in consensus by three board-certified radiologists with expertise in body MRI.

TABLE 1

Parameters of the whole-body MRI sequences

| Sequences | FOV (cm²) Read-Phase | Voxel Size (mm³) Read-Phase-Slice | TR/TE (ms) | Flip Angle (degree) | Scan Time (min/station) | Total Scan Time[a] (min) |
|---|---|---|---|---|---|---|
| DETECT (Coronal) | 30 × 30 (head) 32 × 52 (body) | 1.2 × 1.2 × 5 (head) 1.3 × 1.8 × 5 (body) | 1250/ 70 (TE1), 450 (TE2) | 90 (min)- 100 (mid)- 120 (max) | 1:01 | 7:00 |
| DWIBS (Coronal) | 30 × 30 (head) 32 × 52 (body) | 3.5 × 3.5 × 5 | 12000/70 | NA | 3:09 (head) 3:20 (body) | 16:29 |
| DWIBS (Axial) | 30 × 30 (head) 32 × 52 (body) | 3.5 × 3.5 × 5 | 12000/70 | NA | 3:09 (head) 5:15 (body) | 24:09 |

[a]Five stations and included breathhold instructions for thoracic and abdomen scans for DETECT.

For the most time-efficient imaging of larger FOV, coronal plane acquisitions are often preferred. However, DWIBS images are prone to increased image distortion due to gradient non-linearities in the coronal plane compared to the axial plane. Hence, DWIBS images are commonly acquired in the axial plane to minimize image distortions, but at the expense of increased acquisition times. To evaluate the image quality and acquisition efficiency, one healthy volunteer was scanned with whole-body DWIBS in both axial and coronal planes, compared to whole-body DETECT in the coronal plane. The scan parameters are as listed in Table 1.

Whole-Body Imaging of Patients. Five patients (1 female, age: 58 years; and 4 males, age: 52-68 years) with known mRCC on prior clinical imaging, were scanned to evaluate the performance of DETECT for metastatic cancer detection. The whole-body MRI protocol included DETECT compared against DWIBS using 5 stations in the coronal plane. The acquisition parameters were similar to the above volunteer studies, except for the FOV along the anterior-posterior direction, which varied among subjects between 300-400 mm for complete coverage of the body. To improve the visualization of the metastatic lesions and suppress the signals from complex fluids in the abdomen and bowel, an effective T2 map was generated using the two TE images (Eq. 2), with a threshold of 300 ms. This map effectively suppressed the signals from the complex fluid with moderate T2 values (~300 ms), which were longer than that of the metastatic lesions (~160 ms), but were not long enough to be visible on the long TE image ($TE2_{equiv}$=~400 ms) and therefore, were not suppressed on the DETECT image. Subsequently, a T2map-weighted subtracted image (Eq. 3) was generated to improve the conspicuity and localization of the lesions.

Figure 2A:
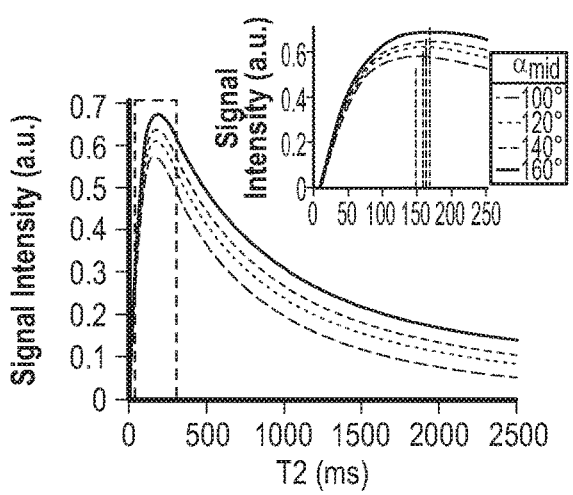
FIGS. 2A to 2D show simulated signal differences between the two different TEs against varying T2 for different refocusing flip angle schemes (FIG. 2A) and partial phase encoding factors (FIG. 2B). The simulation parameters are described in Theory. The maximum signal differences (dashed vertical color lines in insets) shift to longer T2 with the increase of either $\alpha_{mid}$ (FIG. 2a) or partial phase encoding factor (FIG. 2B). A refocusing flip angle train of 90° ($\alpha_{min}$)–100° ($\alpha_{mid}$)–120° ($\alpha_{max}$) shows maximum signal difference for tissues with T2 values between 100 and 200 ms (FIG. 2C). The signal behavior with this scheme shows that the signals from tissues with very long T2 (e.g. CSF and synovial fluid) along with fat appear bright compared to tumor, and need to be suppressed to improve lesion conspicuity (FIG. 2D).
Figure 2B:
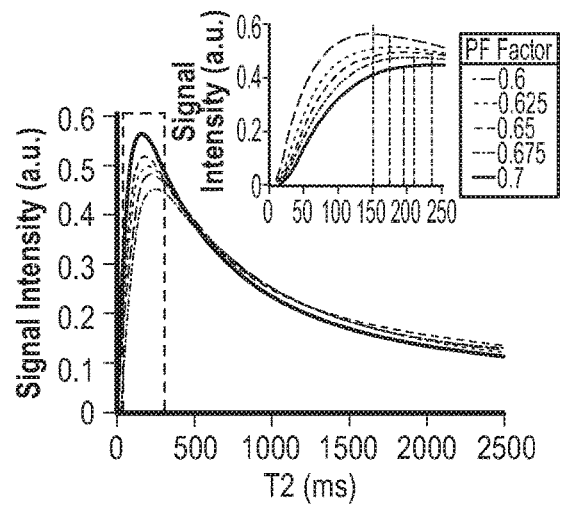
Figure 2C:
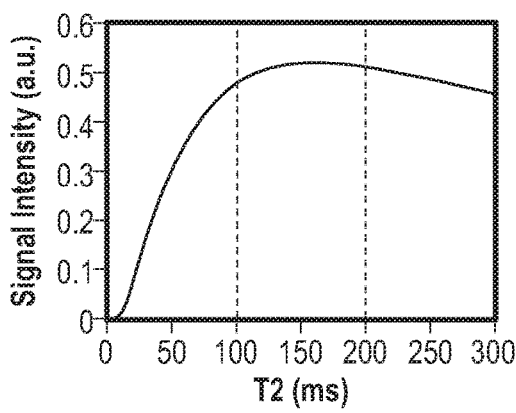
Figure 2D:
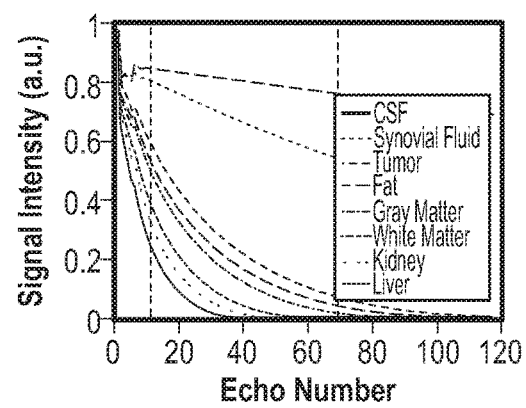

Simulations. FIGS. 2A to 2D show the simulated signal differences between the two TEs of the DETECT with varying refocusing flip angles (FIG. 2A) and partial phase-encoding factors (FIG. 2B). The signal difference for tissues of interest with T2 less than ~160 ms increases with larger $\alpha_{mid}$ (FIG. 2A), but at the expense of increased SAR. The increasing partial phase-encoding factor also increases the relative signal difference for tissues with longer T2 (e.g. 200 ms vs. 150 ms) since it prolongs the $TE_{eff}$ for both TEs (FIG. 2B), but at the expense of reduced SNR. The majority of the tissues in the body (except for fat and fluid) have T2 less than 100 ms at 3 T (28), while the tumors tend to have moderately prolonged T2 but still typically less than 200 ms (32). Thus, an $\alpha_{mid}$ of 100° and partial phase-encoding factor of 0.6 were chosen to retain the T2 contrast of the normal tissues with T2 less than 100 ms on the subtracted DETECT, while maximizing the signal difference for tissues with targeted T2 values around 150 ms (FIG. 2C). This combination, along with $\alpha_{min}$ of 90° and $\alpha_{max}$ of 120°, provided a $TE_{eff}$ of 70 ms for the first TE, matching the clinical whole-body T2W imaging protocol and a $TE_{eff}$ of 450 ms for the second TE, with low SAR (~2.2 W/kg) and reduced sensitivity to motion (22). The simulated signal evolutions of the interested tissues are shown in FIG. 2D. As expected, the fat and fluid appear bright on T2-weighed images and when suppressed using the DETECT, improve the visualization and conspicuity of the tumors.

Figures 3A, 3B, 3C:
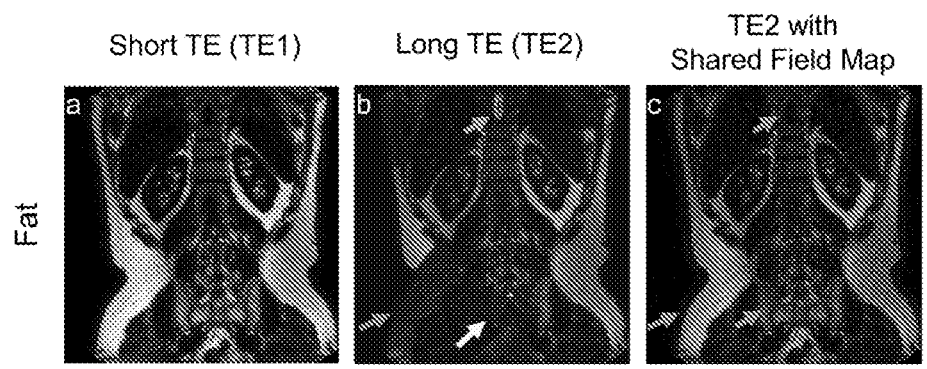
FIGS. 3A to 3F show coronal images of a 47-year-old healthy female volunteer's abdomen showing robust fat/water separation using a standard mDixon reconstruction at the short TE (TE, FIG. 3A, FIG. 3D), and failed fat/water separation at the long TE (TE2, FIG. 3B, FIG. 3E) involving multiple locations (e.g. the subcutaneous fat (red arrows), CSF (green arrow) and bone marrow (yellow arrow)). The shared-field-map mDixon reconstruction (FIG. 3C, FIG. 3F) using the $B_0$ field map from TE1 achieved successful fat/water separation at TE2, even with reduced SNR (blue arrows). Some residual FID artifacts were observed on the fat images due to stimulated echoes, which were subsequently minimized in the whole-body images using stronger crusher gradients.
Figures 3D, 3E, 3F:
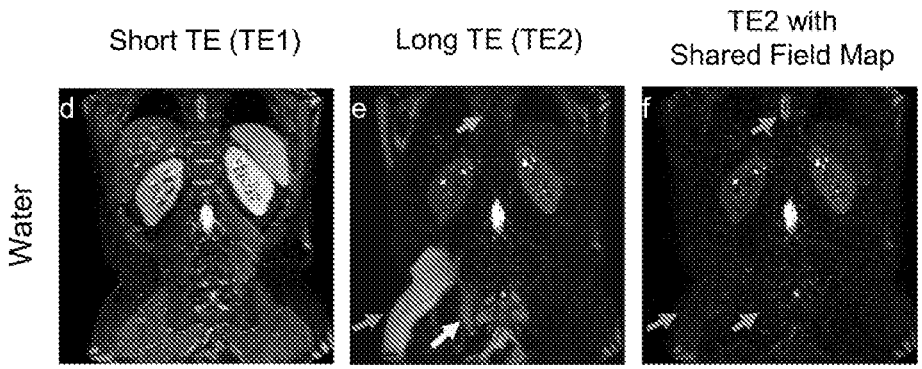
Figures 4A, 4B, 4C:
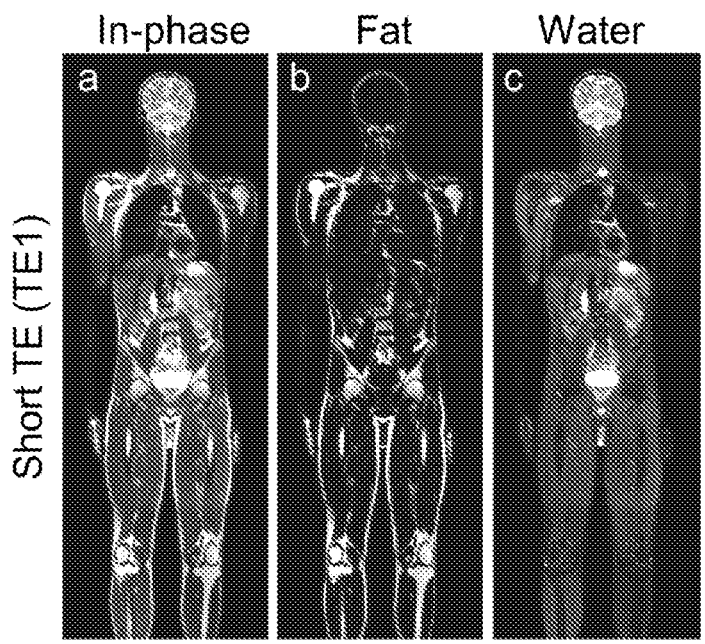
FIGS. 4A to 4G show whole-body MR DETECT images of a 28-year-old healthy male volunteer acquired in five stations in 7 minutes. The standard mDixon reconstruction demonstrates robust fat/water separation across the entire volume at the short TE (FIG. 4A-FIG. 4C), while the shared-field map mDixon reconstruction achieved uniform fat/water separation at long TE (FIG. 4D-FIG. 4F). The subtracted image (FIG. 4G) shows uniform fat and fluid suppression over the entire imaging volume and across all slices.
Figures 4D, 4E, 4F, 4G:
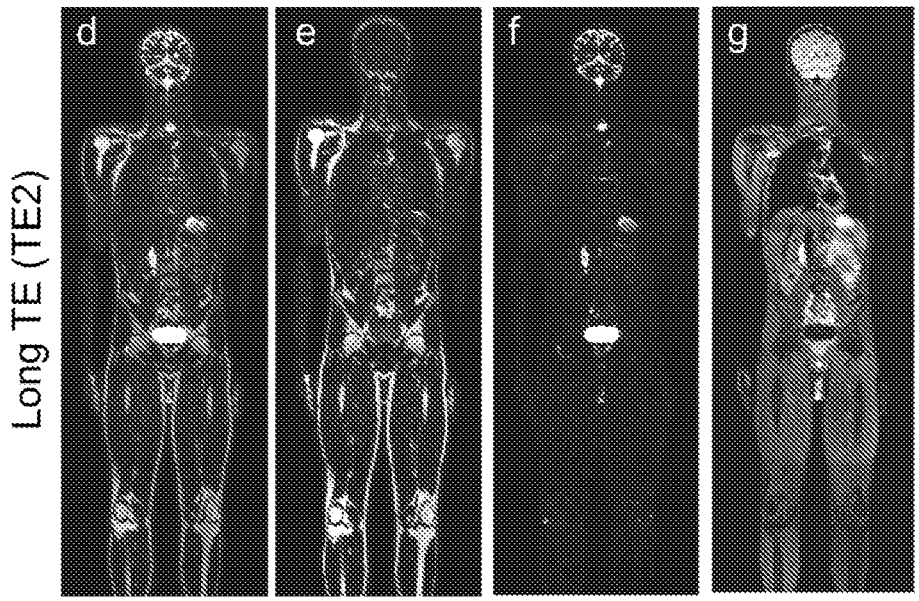

Shared Field-Map mDixon Reconstruction. FIGS. 3A to 3F show the improved fat/water separation in the abdominal images of a 47-year old healthy female volunteer using the shared-field-map mDixon reconstruction. At the short TE (TE1), the standard mDixon reconstruction achieved robust fat/water separation throughout the imaging FOV, with minimum fat/water swaps at the edges of the large FOV (FIGS. 3A, 3D). However, the fat/water separation failed significantly with the standard mDixon reconstruction at the long TE (TE2, FIGS. 3B, 3E) due to the reduced SNR. The proposed shared-field-map mDixon reconstruction using the $B_0$ map from the short TE achieved robust fat/water separation in the long TE images (FIGS. 3C, 3F).

Complex Subtraction. The results of fluid attenuation, reconstructed with both the magnitude and complex subtraction are shown in FIGS. 10A to 10D. The "dark-rim" artifacts, that are often observed around the edges of the tissues with relatively long T2 on magnitude subtraction, are the resultant of the modulation of the point spread function. Since the phase of the water signal is preserved with this phase-preserved homodyne and shared-field-map mDixon reconstruction, the complex subtraction eliminated these "dark-rim" artifacts and resulted in much smoother profiles.

Figures 5A, 5B, 5C:
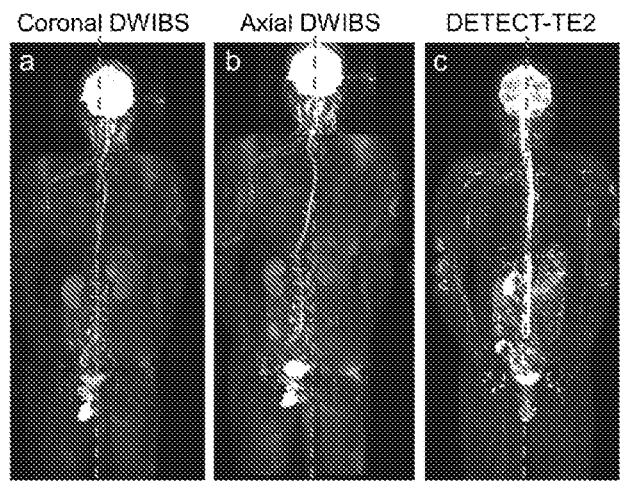
FIGS. 5A to 5C show whole-body 3D MIP reconstructions of a 34-year-old healthy male volunteer demonstrating increased robustness of DETECT to geometric distortions, compared to DWIBS. 3D MIP from coronal DWIBS at b=800 s/mm$^2$ (FIG. 5A) and the coronal reformat from the axial acquisition of DWIBS at b=800 s/mm$^2$ (FIG. 5B) show distorted spinal cord from the midline of the image (red dashed line). 3D MIP of the long TE image from DETECT shows straight spinal canal compared to the midline (FIG. 5C). The DETECT and DWIBS images in the coronal plane across all slices are captured.

Whole-Body Imaging of Normal Volunteers. The shared-field-map mDixon reconstruction and the complex subtraction achieved uniform fat and fluid suppression throughout the body (FIGS. 4A to 4G) and across all slices (data not shown). The whole-body images, acquired with DWIBS in both coronal and axial orientations and with DETECT in coronal orientation are shown in FIGS. 5A, 5B and 5C. DWIBS images in the coronal orientation suffer from large geometric distortions (FIG. 5A). Although the coronal DWIBS images reformatted from the axial acquisitions (FIG. 5B) also suffer from geometric distortions, the originally acquired axial images show less in-plane distortions (not shown). However, the scan times for axial DWIBS acquisitions are generally longer compared to the coronal acquisitions. In this example, the total scan time for the axial DWIBS acquisitions was 19 minutes compared to the 13 minutes for coronal DWIBS acquisitions for 4-station WBMRI. Alternatively, the images acquired using DETECT exhibited minimal geometric distortions (FIG. 5C) in a 6:00 minute coronal plane acquisition for 4-station WBMRI, including breathhold instructions. DETECT images showed better quality with uniform fat and fluid suppression compared to DWIBS without geometric distortions and artifacts in the coronal plane over the entire volume (data not shown).

Figures 6A, 6B, 6C:
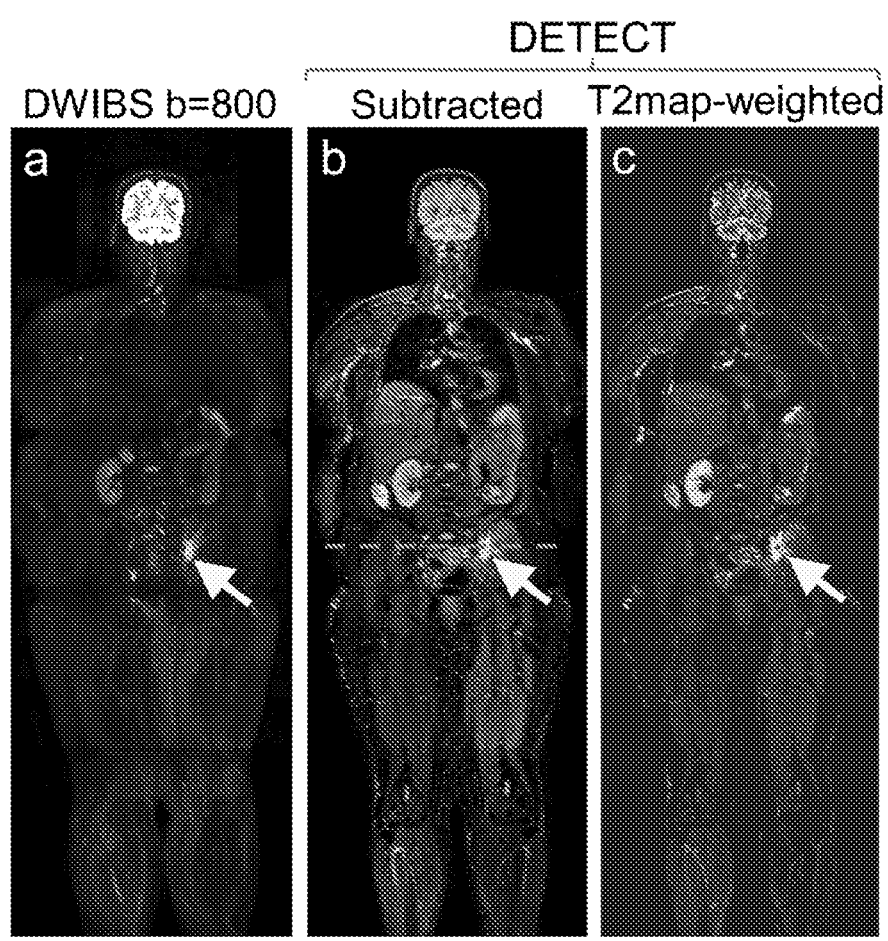
FIGS. 6A to 6F show whole-body MRIs of a 58-year old female patient volunteer with advanced renal cell carcinoma and underwent radiation treatment to the left iliac bone metastatic lesion. DWIBS image at b=800 s/mm$^2$ (FIG. 6A), subtracted DETECT image (FIG. 6B) and the effective T2map-weighted image (FIG. 6C) show conspicuous lesion. Clinical contrast-enhanced fat saturated T1-weighted image of the same patient reveals an enhancing left iliac bone lesion (FIG. 6D, yellow arrow), which also appeared hyper intense on clinical DWI image with b=800 s/mm$^2$ (FIG. 6E, yellow arrow), and ADC map (FIG. 6F) (calculated from 4 b-values; 0, 50, 400, 800 s/mm$^2$), indicative of residual tumor with post-radiation effects.
Figures 6D, 6E, 6F:
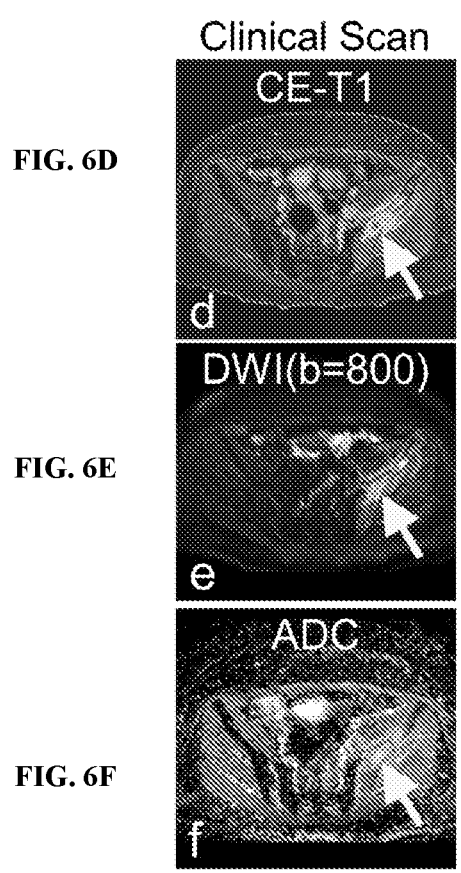
Figures 7A, 7B, 7C:
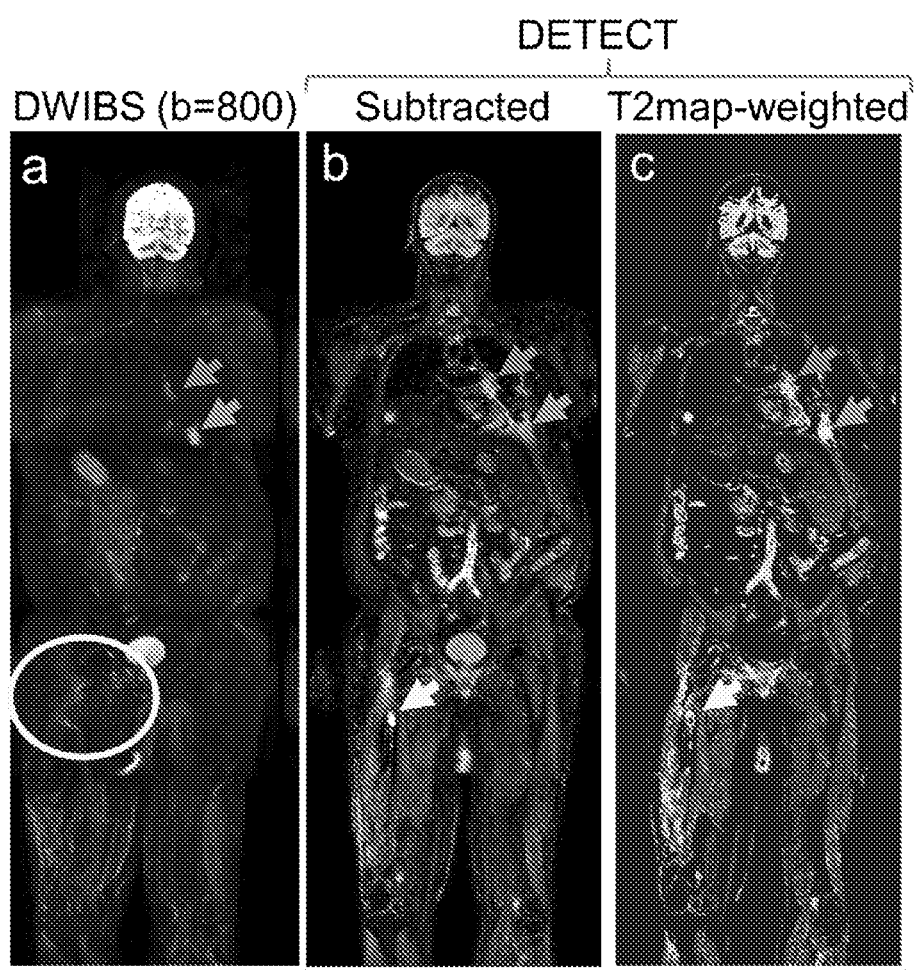
FIGS. 7A to 7C show whole-body MRIs of a 68-year old male patient volunteer with advanced renal cell carcinoma with a history of prophylactic rod placement and radiation treatment for a right femur metastatic lesion: Coronal DWIBS image at b=800 s/mm$^2$ (FIG. 7A), subtracted DETECT image (FIG. 7B), and T2-map weighted image (FIG. 7C) demonstrate metastatic disease involving the left hilum (red arrows) and the left $8^{th}$ rib (green arrows). While a right femur lesion (yellow arrow) is clearly identified on the DETECT images (FIG. 7B, FIG. 7C yellow arrows), it is not visualized on the DWIBS images due to image distortion from the metallic implant (FIG. 7A, yellow circle).

Whole-Body Imaging of Patients. The total number of lesions identified, including lesions per station, on the WB-MRI with DETECT compared to WB-MRI with DWIBS is summarized in Table 2. Overall, the DETECT identified all metastatic lesions known on prior clinical imaging and several additional new lesions, that were not identified on DWIBS due to artifacts associated with severe geometric distortions. For example, both DETECT and DWIBS showed clear delineation of a RCC metastatic lesion in the left iliac bone (FIGS. 6A to 6F), for which the patient was receiving radiation treatment. However, the localization of the lesion with respect to the background anatomy was challenging on the DWIBS image due to the geometric distortions. The subtracted DETECT image, however, retained the lesion signal while suppressing the signals from fat and fluids with long T2 (FIG. 6B). The effective T2-map weighted image, generated with T2 values less than 300 ms, further increased the lesion conspicuity (FIG. 6C). In another mRCC patient with multiple metastatic lesions and right femoral metal implant, DETECT showed improved visualization of the lesions, while the visualization was significantly compromised on the DWIBS images (FIGS. 7A to 7C). Large metastases in the left lung are seen on both DWIBS and DETECT images (red, green arrows, FIGS. 7A to 7C), while DWIBS images suffer from geometric distortions and poor lesion localization. However, the metastatic lesion in the right femur is not visualized on the DWIBS image (yellow circle, FIG. 7A), while it is clearly identified on the DETECT images (yellow arrow, FIGS. 7B, 7C). Similar behavior was observed throughout the entire volume in this patient (data not shown) as well as in other patients (Table 2). Furthermore, the availability of other image contrasts including fat-only image and in-phase image, all acquired in the same sequence and perfectly co-registered, improved the localization of the lesions on DETECT (FIGS. 8A to 8E). Furthermore, the generation of quantitative fat-fraction map (FIG. 8F) allows quantitative and objective measurement of lesion burden and its potential role as a biomarker in assessing treatment response (42).

TABLE 2

Number of lesions identified on WB-MRI with DETECT compared to WB-MRI with DWIBS in patients

| Patient No. | WB-MRI with DETECT Total (per station) | WB-MRI with DWIBS Total (per station) |
|---|---|---|
| 1 | 1 (0/0/0/1/0) | 1 (0/0/0/1/0) |
| 2 | 8 (0/1/2/3/2) | 7 (0/1/2/3/1) |
| 3 | 3 (0/0/3/0/0) | 2 (0/0/2/0/0) |
| 4 | 40 (5/22/5/7/1) | 27 (2/17/3/5/0) |
| 5 | 3 (0/2/1/0/0) | — * |

* Unable to complete WB-MRI DWIBS in patient 5, due to significantly long scan time (~50 minutes)

Additionally, across all 8 whole-body subjects, including 3 healthy volunteers and 5 mRCC patients, the signal of long T2 tissues including, CSF, bile and urine were suppressed by 98±2%, 89±11% and 86±21% respectively.

Whole-body MRI has emerged as a promising clinical option for noninvasive detection of metastatic cancer. The major goals of WB-MRI for cancer detection include, fast imaging, high spatial resolution, and high SNR while simultaneously suppressing the signals from the background tissues to improve the conspicuity of the lesions. While the commonly used WB-MRI technique, DWIBS, provides improved conspicuity of the lesions, it often suffers from poor SNR, low spatial resolution and prolonged acquisition times (9,12,33). Additionally, DWIBS images suffer from geometric distortions, particularly at 3 T, challenging the anatomical localization of the identified lesions.

In this work, the inventors have developed a dual-echo T2-weighted imaging technique for enhanced conspicuity of the tumors (DETECT), that generates fast, high-resolution, and high SNR images with simultaneous fat and fluid suppression, good tumor conspicuity and robustness of RF-refocused spin-echo acquisition in less than 7 minutes scan time for the whole-body imaging. The whole body images can be acquired and processed in less than 16, 15, 14, 13, 12, 11, 10, 9, 8, or 7 minutes. Once the lesions are identified with the proposed DETECT technique, the lesions can be further characterized by dedicated functional MRI techniques such as diffusion, perfusion, hypoxia etc. Due to the use of mDixon acquisition, the DETECT technique also generates perfectly co-registered fat-suppressed T2-weighed images, fat-only images and quantitative fat-fraction map for improved anatomical localization and quantitative assessment of the lesions.

The multi-echo mDixon reconstruction combined with partial-echo acquisitions allowed high resolution T2W imaging with SShTSE in a truly single acquisition, without increasing the scan time compared to SShTSE acquisitions with and without fat suppression. Although, the slight increase in echo spacing (~2.2 ms) due to the acquisition of multi-echo mDixon increased T2 blurring, it was not substantial compared to the standard clinical SShTSE images due to the use of small partial phase encoding factor (0.6), and parallel imaging (×3). However, the fat/water separation often failed at long TE using the standard mDixon reconstruction. Although several algorithms have been developed to improve the fat/water separation, it is still challenging in images with low SNR (24,34,35). This is because the noise increases the uncertainty in solving the phasor ambiguity during the phase-map estimation, especially for dual-echo IP/OP mDixon reconstruction. The shared-field-map mDixon reconstruction used the $B_0$ map from the short TE to overcome this limitation, and achieved uniform fat/water separation on the long TE images. Additionally, the shared field map between the two TEs also reduces the reconstruction times since the phase map estimation is often time consuming and needs to be estimated only once with shared-field-map mDixon reconstruction. Nevertheless, occasional fat/water swaps were noticed on short TE images at the edges of the FOV along the right/left direction (~52 cm FOV). However, these fat/water swaps were minor and restricted to the subcutaneous fat at the far edges of the FOV without affecting the detection of metastatic lesions in this study and can be filtered out.

The complex signal modeled by this phase-preserved homodyne reconstruction and the shared-field-map mDixon reconstruction allowed complex subtraction between the two water-only images. This complex subtraction eliminated the "dark-rim" artifacts, observed in the magnitude-subtracted water-only images. Since the fluid-like tissues have longer T2s, the Gibbs ringing artifacts observed with Cartesian view ordering are larger in images acquired with partial phase-encoding and partial readout than those acquired with full k-space. This amplifies the side lobes in PSF on magnitude images, which are cancelled out by the complex subtraction and thus eliminating the "dark-rim" artifacts.

Short tau inversion recovery (STIR) is the most commonly used fat suppression method in WB-MRI due to its insensitivity to B0 inhomogeneities. However, STIR pulse(s) imparts a mix of T1 and T2 contrast and thus, a T2W imaging sequence is typically included in the WB-MRI protocol. Compared to this, the DETECT imaging technique disclosed herein for the first time simultaneously provides standard T2W images with and without fat suppression in addition to the fat and fluid suppressed T2W images, all of them perfectly co-registered to each other, without increasing the total scan times as a consequence of the data for both TEs being acquired within the same excitation.

Whole-body DWIBS has been increasingly used for the detection of metastatic lesions, since the DWIBS images have increased lesion conspicuity (12,37). However, DWIBS images suffer from increased geometric distortions, combined with chemical shift artifacts and larger voxel size. Hence, the majority of DWIBS protocols are currently performed at 1.5 T for whole-body imaging, necessitating longer scan times to compensate for the reduced SNR (12,38-40). Compared to DWIBS, the DETECT imaging technique of the present invention provided images with superior SNR and higher spatial resolution in shorter scan times at 3 T. Although the lesion-to-background conspicuity was not superior with DETECT compared to DWIBS, it generated images with fewer artifacts and minimal geometric distortions even in the presence of metal implants (e.g. FIGS. 7A to 7C), making it more reliable. Due to the shorter acquisition times of less than 7 minutes for whole-body imaging, the DETECT imaging technique can also be performed in multiple orientations, if needed, to improve the lesion localization. Furthermore, DETECT imaging technique can be an appealing alternative technique for whole-body imaging, with the increasing availability of 3 T scanners.

FIG. 9 shows a flowchart showing the DETECT reconstruction including fat and fluid suppression and quantitative fat-fraction map generation. The method 100 begins with the acquisition of 4 echoes following a single excitation 102. Next, two echoes at a short TE 104 are processed into an IP image 108 and an OP image 110, which are processed through standard mDixon reconstruction 112. Concurrently, two echoes at the long TE 106 are obtained and separated into an IP image 114 and an OP image 116, which are the processed through shared-Field-Map mDixon reconstruction 118. The phase map from the Standard mDixon 112 is used with the shared-Field-Map mDixon 118. The standard mDixon 112 processes the IP image 108 and the OP image 110 into the water-only image at TE1 120 and the Fat only image at TE1 122. Using the Water-only image at TE1 120 and the fat-only image at TE1 122, a quantitative fat-fraction map 128 can be obtained by dividing the fat-only image by the sum of water-only image 120 and fat-only image 122. The shared-Field-Map mDixon 118 processes the IP image 114 and the OP image 116 into a water-only image at TE2 124 and a fat-only image at TE2 126. The water-only image at TE2 124 is subtracted from the water-only image at TE1 120 to obtain the fat- and fluid-suppressed DETECT image 130.

Figure 10A:
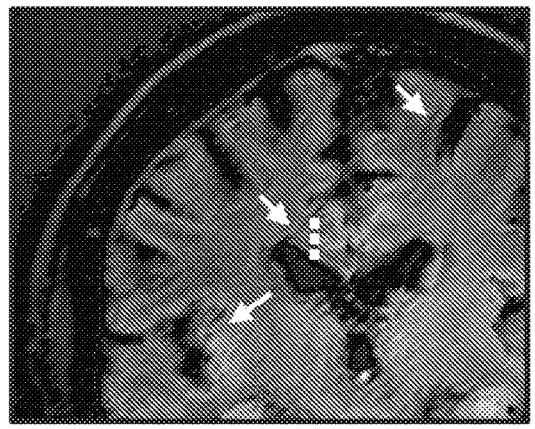
FIGS. 10A to 10D show subtracted brain images of a 62-year-old healthy male volunteer showing "dark-rim" artifacts with magnitude subtraction (FIG. 10A, white arrows), which are eliminated with complex subtraction (FIG. 10B). In long TE images, the first side lobes of the point spread function of hyper-intense tissues are often negative due to the heavy signal decay of the surrounding tissues. The magnitude operation converts these negative local minima into positive local maxima (FIG. 10C, red arrow), which manifest as local minima on magnitude-subtracted images (FIG. 10C, black arrow) and create "dark-rim" artifacts (FIG. 10A, white arrows). The signal profiles (FIG. 10C, FIG. 10D) corresponding to the dashed red lines in (FIG. 10A, FIG. 10B) show the local maxima of the magnitude profile on TE2 image (FIG. 10C, red arrow), that create the local minima on the magnitude subtracted profile (FIG. 10C, black arrow), and are rectified in complex subtraction (FIG. 10D).
Figure 10B:
Figure 10C:
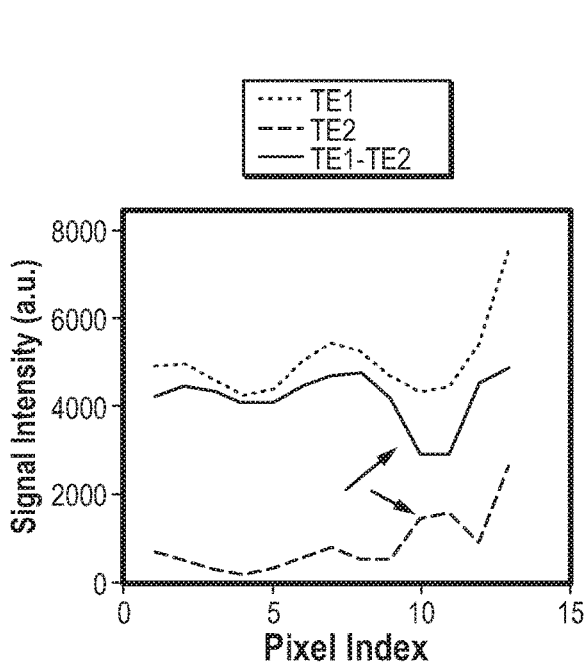
Figure 10D:
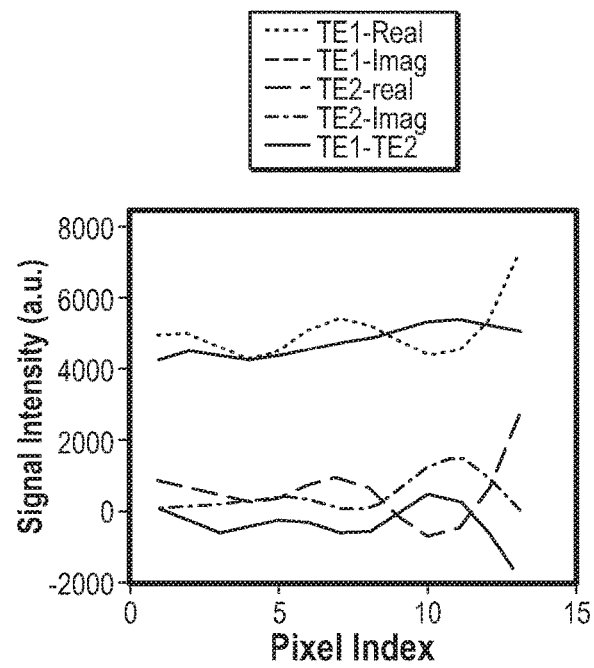

FIGS. 10A to 10D show subtracted brain images of a 62-year-old healthy male volunteer showing "dark-rim" artifacts with magnitude subtraction (FIG. 10A, white arrows), which are eliminated with complex subtraction (FIG. 10B). In long TE images, the first side lobes of the point spread function of hyper-intense tissues are often negative due to the heavy signal decay of the surrounding tissues. The magnitude operation converts these negative local minima into positive local maxima (FIG. OC, red arrows), which manifest as local minima on magnitude-subtracted images (FIG. 10C, black arrow) and create "dark-rim" artifacts (FIG. 10A, white arrows). The signal profiles (FIG. 10C, FIG. 10D) corresponding to the dashed red lines in (FIG. 10A, FIG. 10B) show the local maxima of the magnitude profile on TE2 image (FIG. 10C, red arrow), that create the local minima on the magnitude subtracted profile (FIG. 10C, black arrow), and are rectified in complex subtraction (FIG. 10D).

Figure 11:
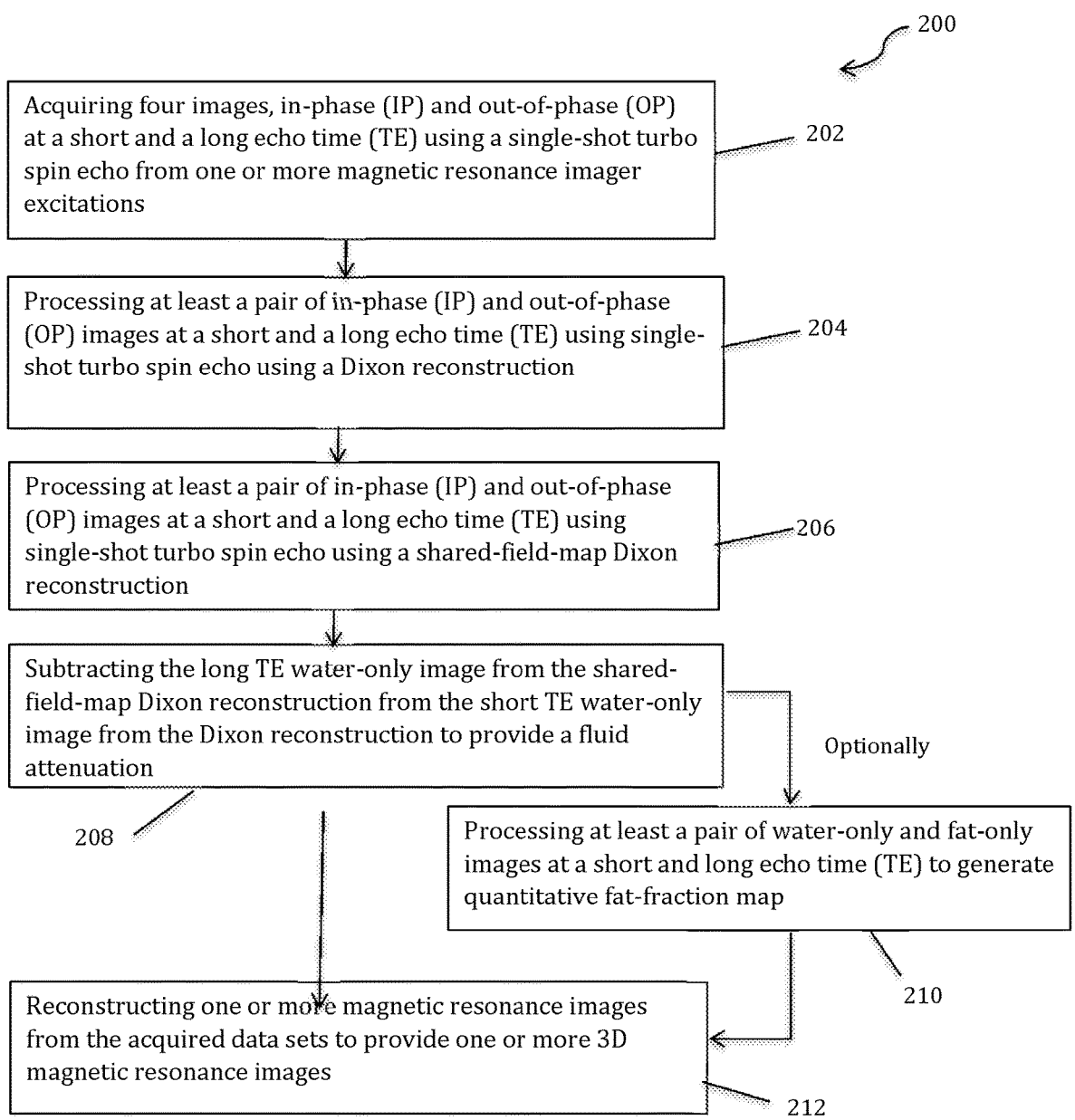
FIG. 11 is a flowchart 200 that summarizes the basic method of the present invention.

FIG. 11 is a flowchart 200 that summarizes the basic method of the present invention. In step 202, the method begins by acquiring four images, in-phase (IP) and out-of-phase (OP) at a short and a long echo time (TE) using a single-shot turbo spin echo from one or more magnetic resonance imager excitations. In step 204, the method includes processing at least a pair of in-phase (IP) and out-of-phase (OP) images at a short and a long echo time (TE) using single-shot turbo spin echo using a Dixon reconstruction. In step 206, the method includes processing at least a pair of in-phase (IP) and out-of-phase (OP) images at a short and a long echo time (TE) using single-shot turbo spin echo using a shared-field-map Dixon reconstruction. In step 208, the method includes subtracting the long TE water-only image from the shared-field-map Dixon reconstruction from the short TE water-only image from the Dixon reconstruction to provide a fluid attenuation. An optional step 210 includes processing at least a pair of water-only and fat-only images at a short and long echo time (TE) to generate quantitative fat-fraction map. Finally, in step 212, the method includes reconstructing one or more magnetic resonance images from the acquired data sets to provide one or more 3D magnetic resonance images.

In conclusion, the inventors have developed a fast, high-resolution, and high SNR T2-weighted imaging with simultaneous fat and fluid suppression, called DETECT, for whole-body MRI at 3 T. Compared to the commonly used DWIBS for whole-body MRI, DETECT can be performed in significantly shorter scan times (17 min. vs. 7 min.) and generates images with good lesion conspicuity, and without the image distortion associated with EPI. This sequence can serve as an initial imaging technique for whole-body cancer detection, followed by characterization of selected tumors by dedicated functional MR imaging.

The present invention can also be used to measure real-time ablation volumes, that can be interleaved with real-time temperature monitoring in Magnetic resonance imaging (MRI) guided ablation therapies. MRI guided ablation is increasingly used for targeted therapies. For example, thermal ablation using MRI guided high-intensity focused ultrasound (MRg-HIFU) can be used to treat uterine fibroids, central neuropathic pain, tremors, brain tumors etc. and MRI guided cryoablation can be used for treating prostate cancer. Thermal (or cryo) ablation produces cell death in targeted areas by heating (or cooling) the local area with minimal damage to the surrounding tissue. MRI guidance allows for the monitoring of the temperature changes, in near real-time allowing quantification of the therapeutic dose. However, MRI acquisition times of the currently existing techniques are too long to provide real-time anatomic images to complement real-time temperature mapping. The present invention described above allows for the acquisition of real-time anatomic MR images in less than a second that can be interleaved with real-time temperature measurement for accurate monitoring of MRI guided ablation therapies.

Furthermore, the present invention overcomes problems with the most commonly used method for measuring ablation volume, which is the use of post-contrast images following the administration of a Gadolinium based contrast agent. A significant challenge with this prior art approach is that, post-contrast images can only be acquired at the conclusion of the ablation therapy and cannot be interleaved with ablation treatment. The presence of a contrast agent in the targeted area introduces errors in the MR temperature mapping performed during ablation treatment. Compared to this, the DETECT approach does not use contrast injection and can be used during the ablation therapy providing real-time measurements of ablation volume. Additionally, the DETECT approach also has several advantages compared to the existing MRI techniques such as turbo spin echo (TSE), gradient echo (GRE) and/or echo planar imaging (EPI) that can be used to measure ablation volume.

First, TSE images typically can be acquired in few seconds to minutes. Compared to TSE, the DETECT images can be acquired in less than a second, allowing for real-time volume measurement. Additionally, the DETECT method integrated with mDixon approach provides images with uniform fat suppression even in the presence of increased $B_0$ inhomogeneities, making it robust for body applications including abdomen and pelvis. Second, compared to GRE images, the DETECT approach provides T2-weighted contrast, which is more relevant to observe the acute ablation changes such as accumulation of fluid/edema, without the administration of gadolinium based contrast agents. Third, EPI images can be acquired in relatively shorter acquisition times, however, are more sensitive to image artifacts in the abdomen/pelvic applications due to larger fields of view and are confounded by fat signal. Compared to EPI, the DETECT approach is more robust in larger fields of view with efficient and uniform fat suppression allowing more accurate representation of the anatomy.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

1. Antoch G, Saoudi N, Kuehl H, Dahmen G, Mueller S P, Beyer T, Bockisch A, Debatin Jr F, Freudenberg L S. Accuracy of whole-body dual-modality fluorine-18-2-fluoro-2-deoxy-D-glucose positron emission tomography and computed tomography (FDG-PET/CT) for tumor staging in solid tumors: comparison with CT and PET. J Clin Oncol 2004; 22(21):4357-4368.
2. Schöder H, Gönen M. Screening for cancer with PET and PET/CT: potential and limitations. J Nucl Med 2007; 48(1 suppl):4S-18S.
3. Hall E, Brenner D. Cancer risks from diagnostic radiology. Br J Radiol 2008; 81(965):362-378.
4. Klenk C, Gawande R, Uslu L, Khurana A, Qiu D, Quon A, Donig J, Rosenberg J, Luna-Fineman S, Moseley M. Ionising radiation-free whole-body MRI versus 18 F-fluorodeoxyglucose PET/CT scans for children and young adults with cancer: a prospective, non-randomised, single-centre study. Lancet Oncol 2014; 15(3):275-285.
5. Park J-W, Kim J H, Kim S K, Kang K W, Park K W, Choi J-I, Lee W J, Kim C-M, Nam B H. A prospective evaluation of 18F-FDG and 11C-acetate PET/CT for detection of primary and metastatic hepatocellular carcinoma. J Nucl Med 2008; 49(12):1912-1921.
6. Nomori H, Watanabe K, Ohtsuka T, Naruke T, Suemasu K, Uno K. Evaluation of F-18 fluorodeoxyglucose (FDG) PET scanning for pulmonary nodules less than 3 cm in diameter, with special reference to the CT images. Lung Cancer 2004; 45(1):19-27.
7. Kim S M, Cha R-h, Lee J P, Kim D K, Oh K-H, Joo K W, Lim C S, Kim S, Kim Y S. Incidence and outcomes of contrast-induced nephropathy after computed tomography in patients with CKD: a quality improvement report. Am J Kidney Dis 2010; 55(6):1018-1025.
8. Schmidt G P, Reiser M F, Baur-Melnyk A. Whole-body MRI for the staging and follow-up of patients with metastasis. Eur J Radiol 2009; 70(3):393-400.
9. Takenaka D, Ohno Y, Matsumoto K, Aoyama N, Onishi Y, Koyama H, Nogami M, Yoshikawa T, Matsumoto S, Sugimura K. Detection of bone metastases in non-small cell lung cancer patients: Comparison of whole-body diffusion-weighted imaging (DWI), whole-body MR imaging without and with DWI, whole-body FDG-PET/CT, and bone scintigraphy. J Magn Reson Imaging 2009; 30(2):298-308.
10. Kwee T C, Takahara T, Ochiai R, Nievelstein R A, Luijten P R. Diffusion-weighted whole-body imaging with background body signal suppression (DWIBS): features and potential applications in oncology. Eur Radiol 2008; 18(9):1937-1952.
11. Eiber M, Holzapfel K, Ganter C, Epple K, Metz S, Geinitz H, Kübler H, Gaa J, Rummeny E J, Beer A J. Whole-body MRI including diffusion-weighted imaging (DWI) for patients with recurring prostate cancer: Technical feasibility and assessment of lesion conspicuity in DWI. J Magn Reson Imaging 2011; 33(5):1160-1170.
12. Koh D-M, Blackledge M, Padhani A R, Takahara T, Kwee T C, Leach M O, Collins D J. Whole-body diffusion-weighted MRI: tips, tricks, and pitfalls. Am J Roentgenol 2012; 199(2):252-262.
13. Walker R, Kessar P, Blanchard R, Dimasi M, Harper K, DeCarvalho V, Yucel E, Patriquin L, Eustace S. Turbo STIR magnetic resonance imaging as a whole-body screening tool for metastases in patients with breast carcinoma: Preliminary clinical experience. J Magn Reson Imaging 2000; 11(4):343-350.
14. Punwani S, Taylor S A, Bainbridge A, Prakash V, Bandula S, De Vita E, Olsen O E, Hain S F, Stevens N, Daw S. Pediatric and Adolescent Lymphoma: Comparison of Whole-Body STIR Half-Fourier RARE MR Imaging with an Enhanced PET/CT Reference for Initial Staging 1. Radiology 2010; 255(1):182-190.
15. Del Grande F, Santini F, Herzka D A, Aro M R, Dean C W, Gold G E, Carrino J A. Fat-suppression techniques for 3-T MR imaging of the musculoskeletal system. Radiographics 2014; 34(1):217-233.
16. Schwartz L, Seltzer S, Tempany C, Silverman S, Piwnica-Worms D, Adams D, Herman L, Herman L, Hooshmand R. Prospective comparison of T2-weighted fast spin-echo, with and without fat suppression, and conventional spin-echo pulse sequences in the upper abdomen. Radiology 1993; 189(2):411-416.
17. Jackson A, Sheppard S, Johnson A C, Annesley D, Laitt R D, Kassner A. Combined fat- and water-suppressed MR imaging of orbital tumors. Am J Neuroradiol 1999; 20(10):1963-1969.

18. Lauenstein T C, Sharma P, Hughes T, Heberlein K, Tudorascu D, Martin D R. Evaluation of optimized inversion-recovery fat-suppression techniques for T2-weighted abdominal MR imaging. J Magn Reson Imaging 2008; 27(6):1448-1454.
19. Wang X, Greer J S, Pedrosa I, Rofsky N M, Madhuranthakam A J. Robust abdominal imaging with uniform fat suppression using Dixon based single shot turbo spin echo. In Proceedings of the 24th Annual Meeting of ISMRM. Singapore, 2016. p. 573.
20. Essig M, Deimling M, Hawighorst H, Debus J, van Kaick G. Assessment of cerebral gliomas by a new dark fluid sequence, high intensity Reduction (HIRE): a preliminary study. J Magn Reson Imaging 2000; 11(5):506-517.
21. Madhuranthakam A J, Lee K S, Yassin A, Brittain J H, Pedrosa I, Rofsky N M, Alsop D C. Improved short tau inversion recovery (iSTIR) for increased tumor conspicuity in the abdomen. Magn Reson Mater Phy 2014; 27(3):245-255.
22. Loening A M, Saranathan M, Ruangwattanapaisarn N, Litwiller D V, Shimakawa A, Vasanawala S S. Increased speed and image quality in single-shot fast spin echo imaging via variable refocusing flip angles. J Magn Reson Imaging 2015; 42(6):1747-1758.
23. Wang X, Harrison C, Mariappan Y K, Gopalakrishnan K, Chhabra A, Lenkinski R E, Madhuranthakam A J. MR Neurography of Brachial Plexus at 3.0 T with Robust Fat and Blood Suppression. Radiology 2017; 283(2):538-546.
24. Eggers H, Brendel B, Duijndam A, Herigault G. Dual-echo Dixon imaging with flexible choice of echo times. Magn Reson Med 2011; 65(1):96-107.
25. Wang X, Greer J S, Pinho M C, Lenkinski R E, Madhuranthakam A J. Volumetric T2-weighted and FLAIR Imaging of Spine with Uniform Fat Suppression in a Single Acquisition. In Proceedings of the 25th Annual Meeting of ISMRM. Honolulu, Hawaii, USA, 2017. p. 191.
26. Busse R F, Brau A, Vu A, Michelich C R, Bayram E, Kijowski R, Reeder S B, Rowley H A. Effects of refocusing flip angle modulation and view ordering in 3D fast spin echo. Magn Reson Med 2008; 60(3):640-649.
27. Sarkar S N, Alsop D C, Madhuranthakam A J, Busse R F, Robson P M, Rofsky N M, Hackney D B. Brain MR imaging at ultra-low radiofrequency power. Radiology 2011; 259(2):550-557.
28. Stanisz G J, Odrobina E E, Pun J, Escaravage M, Graham S J, Bronskill M J, Henkelman R M. T1, T2 relaxation and magnetization transfer in tissue at 3 T. Magn Reson Med 2005; 54(3):507-512.
29. Gold G E, Han E, Stainsby J, Wright G, Brittain J, Beaulieu C. Musculoskeletal MRI at 3.0 T: relaxation times and image contrast. Am J Roentgenol 2004; 183(2):343-351.
30. Smith S A, Edden R A, Farrell J A, Barker P B, Van Zijl P. Measurement of T1 and T2 in the cervical spinal cord at 3 tesla. Magn Reson Med 2008; 60(1):213-219.
31. De Bazelaire C M, Duhamel G D, Rofsky N M, Alsop D C. MR imaging relaxation times of abdominal and pelvic tissues measured in vivo at 3.0 T: preliminary results. Radiology 2004; 230(3):652-659.
32. Badve C, Yu A, Dastmalchian S, Rogers M, Ma D, Jiang Y, Margevicius S, Pahwa S, Lu Z, Schluchter M. MR Fingerprinting of Adult Brain Tumors: Initial Experience. Am J Neuroradiol 2017; 38(3):492-499.
33. Inada Y, Matsuki M, Nakai G, Tatsugami F, Tanikake M, Narabayashi I, Yamada T, Tsuji M. Body diffusion-weighted MR imaging of uterine endometrial cancer: is it helpful in the detection of cancer in nonenhanced MR imaging? Eur J Radiol 2009; 70(1):122-127.
34. Ma J, Son J B, Hazle J D. An improved region growing algorithm for phase correction in MRI. Magn Reson Med 2016; 76(2):519-529.
35. Berglund J, Ahlström H, Johansson L, Kullberg J. Two-point dixon method with flexible echo times. Magn Reson Med 2011; 65(4):994-1004.
36. Stinson E G, Trzasko J D, Fletcher J G, Riederer S J. Dual echo Dixon imaging with a constrained phase signal model and graph cuts reconstruction. Magn Reson Med 2017; 78(6):2203-2215.
37. Padhani A R, Koh D-M, Collins D J. Whole-body diffusion-weighted MR imaging in cancer: current status and research directions. Radiology 2011; 261(3):700-718.
38. Lavdas I, Rockall A G, Castelli F, Sandhu R S, Papadaki A, Honeyfield L, Waldman A D, Aboagye E O. Apparent diffusion coefficient of normal abdominal organs and bone marrow from whole-Body DWI at 1.5 T: the effect of sex and age. Am J Roentgenol 2015; 205(2):242-250.
39. Jambor I, Kuisma A, Ramadan S, Huovinen R, Sandell M, Kajander S, Kemppainen J, Kauppila E, Auren J, Merisaari H. Prospective evaluation of planar bone scintigraphy, SPECT, SPECT/CT, 18F—NaF PET/CT and whole body 1.5 T MRI, including DWI, for the detection of bone metastases in high risk breast and prostate cancer patients: SKELETA clinical trial. Acta Oncol 2016; 55(1): 59-67.
40. Kwee T C, Takahara T, Ochiai R, Katahira K, Van Cauteren M, Imai Y, Nievelstein R A, Luijten P R. Whole-body diffusion-weighted magnetic resonance imaging. Eur J Radiol 2009; 70(3):409-417.
41. Lu H, Ge Y. Quantitative evaluation of oxygenation in venous vessels using T2-Relaxation-Under-Spin-Tagging MRI. Magn Reson Med 2008; 60(2):357-363.
42. Latifoltojar A, Hall-Craggs M, Bainbridge A, et al. Whole-body MRI quantitative biomarkers are associated significantly with treatment response in patients with newly diagnosed symptomatic multiple myeloma following bortezomib induction. Eur Radiol 2017; 27:5325-36.

What is claimed is:

1. A method for magnetic resonance imaging with simultaneous fat and fluid suppression of a subject comprising:
   acquiring four images, or data sets of images, in-phase (IP) and out-of-phase (OP) at a short and a long echo time (TE) using a single-shot turbo spin echo from one or more magnetic resonance imager excitations:
   processing at least a pair of in-phase (IP) and out-of-phase (OP) images at a short and a long echo time (TE) using single-shot turbo spin echo using a Dixon reconstruction;
   processing at least a pair of in-phase (IP) and out-of-phase (OP) images at a short and a long echo time (TE) using single-shot turbo spin echo using a shared-field-map Dixon reconstruction;
   subtracting a long TE water-only image from the shared-field-map Dixon reconstruction from the short TE water-only image from the Dixon reconstruction to provide a fluid attenuation; and
   reconstructing one or more magnetic resonance images from the acquired four images or data sets into one or more 3D magnetic resonance images.

2. The method of claim 1, further comprising the step of processing at least a pair of water-only and fat-only images at a short and long echo time (TE) to generate a quantitative fat-fraction map between the step of subtracting the long TE water-only image and reconstructing one or more magnetic resonance images.

3. The method of claim 1, wherein the magnetic resonance images of a single slice are acquired in less than one second, or with a 1.5 T or 3 T magnetic resonance imager.

4. The method of claim 1, wherein the four images are at least one of whole body images, lesions suspected of being a cancer, or cancer lesions.

5. The method of claim 1, wherein a processing time for a fluid attenuated whole body image is less than 16, 15, 14, 13, 12, 11, 10, 9, 8, or 7 minutes.

6. The method of claim 1, wherein each pair of in-phase (IP) and out-of-phase (OP) images are captured after a single 90° excitation pulse, with a short TE (TE1, ~60-80 ms) and long TE (TE2, ~400 ms).

7. The method of claim 1, further comprising at least one of: (1) capturing echoes between each pair of refocusing pulses for each pair of in-phase (IP) and out-of-phase (OP) images, (2) creating a shared-field-map mDixon reconstruction in which a B0 map estimated at the short TE is used for fat/water separation at the long TE; or (3) performing an adaptive complex subtraction of the long TE water-only image from the short TE water-only image to achieve fluid attenuation.

8. The method of claim 1, wherein the method simultaneously suppresses fat and fluid in the images.

9. The method of claim 1, wherein each pair of in-phase (IP) and out-of-phase (OP) images are acquired in a single repetition using variable refocusing flip angles and partial phase-encoding acquisitions using the single shot turbo spin echo.

10. The method of claim 1, further comprising a division of a fat-only image by a sum of a water-only and fat-only image at short TE to generate a quantitative fat-fraction map.

11. The method of claim 1, wherein a magnetic resonance image is interleaved with a real-time temperature measurement for accurate monitoring of MRI guided ablation therapies.

12. The method of claim 1, wherein the long TE water-only image shows an ablation volume in MRI guided ablation therapies.

13. A method of three dimensional (3D) dynamic magnetic resonance imaging of an imaging space comprising:
placing a subject into a substantially homogeneous magnetic field in the imaging space of a magnetic resonance imager;
acquiring four images, or data sets of images, in-phase (IP) and out-of-phase (OP) at a short and a long echo time (TE) using a single-shot turbo spin echo from one or more magnetic resonance imager excitations;
processing at least a pair of in-phase (IP) and out-of-phase (OP) images at a short and a long echo time (TE) using single-shot turbo spin echo using a Dixon reconstruction;
processing at least a pair of in-phase (IP) and out-of-phase (OP) images at a short and a long echo time (TE) using single-shot turbo spin echo using a shared-field-map Dixon reconstruction;
subtracting a long TE water-only image from the shared-field-map Dixon reconstruction from the short TE water-only image from the Dixon reconstruction to provide a fluid attenuation;
processing at least a pair of water-only and fat-only images at a short and long echo time (TE) to generate a quantitative fat-fraction map; and
reconstructing one or more magnetic resonance images from the acquired four images or data sets into one or more 3D magnetic resonance images.

14. The method of claim 12, further comprising a division of a fat-only image by a sum of a water-only and fat-only image at short TE to generate a quantitative fat-fraction map.

15. The method of claim 12, wherein a magnetic resonance image is interleaved with a real-time temperature measurement for accurate monitoring of MRI guided ablation therapies.

16. The method of claim 12, wherein the long TE water-only image shows an ablation volume in MRI guided ablation therapies.

17. A computerized method of three dimensional (3D) dynamic magnetic resonance imaging, the method comprising:
acquiring four images, or data sets of images, in-phase (IP) and out-of-phase (OP) at a short and a long echo time (TE) using a single-shot turbo spin echo from one or more magnetic resonance imager excitations; and
using a processor:
processing at least a pair of in-phase (IP) and out-of-phase (OP) images at a short and a long echo time (TE) using single-shot turbo spin echo using a Dixon reconstruction;
processing at least a pair of in-phase (IP) and out-of-phase (OP) images at a short and a long echo time (TE) using single-shot turbo spin echo using a shared-field-map Dixon reconstruction;
subtracting a long TE water-only image from the shared-field-map Dixon reconstruction from the short TE water-only image from the Dixon reconstruction to provide a fluid attenuation;
processing at least a pair of water-only and fat-only images at a short and long echo time (TE) to generate a quantitative fat-fraction map; and
reconstructing one or more magnetic resonance images from the acquired data sets to provide one or more 3D magnetic resonance images.

18. A system for three dimensional (3D) dynamic magnetic resonance imaging, the system comprising:
a magnetic resonance imager that generates a substantially homogeneous magnetic field in an imaging space and capable of detecting a subject for magnetic resonance imaging; and
a processor comprising a non-transitory computer readable medium comprising instructions stored thereon for:
acquiring four images, or data sets of images, in-phase (IP) and out-of-phase (OP) at a short and a long echo time (TE) using a single-shot turbo spin echo from one or more magnetic resonance imager excitations;
processing at least a pair of in-phase (IP) and out-of-phase (OP) images at a short and a long echo time (TE) using single-shot turbo spin echo using a Dixon reconstruction;
processing at least a pair of in-phase (IP) and out-of-phase (OP) images at a short and a long echo time (TE) using single-shot turbo spin echo using a shared-field-map Dixon reconstruction;
subtracting a long TE water-only image from the shared-field-map Dixon reconstruction from the short TE water-only image from the Dixon reconstruction to provide a fluid attenuation;
processing at least a pair of water-only and fat-only images at a short and long echo time (TE) to generate a quantitative fat-fraction map; and reconstructing the one or more magnetic resonance images from the acquired data sets to provide one or more 3D magnetic resonance images;

wherein the processor reconstructs the one or more magnetic resonance images from the acquired four images or data sets to provide a set of 3D magnetic resonance images with a processor, wherein the 3D magnetic resonance images are obtained without increasing sensitivity to B0 inhomogeneities, and simultaneously suppressing fat and fluid in the images; and storing on a computer or in one or more databases or displaying on a communications interface, the 3D magnetic resonance images.

\* \* \* \* \*